(12) United States Patent
Rottmann et al.

(10) Patent No.: US 11,911,178 B2
(45) Date of Patent: Feb. 27, 2024

(54) SYSTEM AND METHOD TO DETECT AND TREAT ARRHYTHMOGENIC REGIONS IN ATRIAL FIBRILLATION

(71) Applicant: Northwestern University, Evanston, IL (US)

(72) Inventors: Markus Rottmann, Chicago, IL (US); Rishi K. Arora, Chicago, IL (US); David A. Johnson, Romeoville, IL (US); Shin Yoo, Wilmette, IL (US)

(73) Assignee: Northwestern University, Evanston, IL (US)

( * ) Notice: Subject to any disclaimer, the term of this patent is extended or adjusted under 35 U.S.C. 154(b) by 365 days.

(21) Appl. No.: 17/308,756

(22) Filed: May 5, 2021

(65) Prior Publication Data

US 2021/0345958 A1   Nov. 11, 2021

Related U.S. Application Data

(60) Provisional application No. 63/111,282, filed on Nov. 9, 2020, provisional application No. 63/040,244, filed
(Continued)

(51) Int. Cl.
*A61B 5/00* (2006.01)
*A61B 5/361* (2021.01)
(Continued)

(52) U.S. Cl.
CPC ............ *A61B 5/4848* (2013.01); *A61B 5/339* (2021.01); *A61B 5/361* (2021.01); *A61K 31/198* (2013.01); *G16H 50/20* (2018.01); *G16H 50/30* (2018.01)

(58) Field of Classification Search
CPC ....... A61B 5/4848; A61B 5/339; A61B 5/361; A61K 31/198; G16H 50/20; G16H 20/10
See application file for complete search history.

(56) References Cited

U.S. PATENT DOCUMENTS

2005/0209524 A1   9/2005   Donaldson et al.
2010/0094274 A1   4/2010   Narayan et al.
(Continued)

FOREIGN PATENT DOCUMENTS

WO   WO 2011/044230 A2   4/2011

OTHER PUBLICATIONS

The International Search Report and the Written Opinion dated Sep. 9, 2021 for International application No. PCT/US2021/030889; pp. 1-12.
(Continued)

*Primary Examiner* — Mallika D Fairchild
*Assistant Examiner* — Shreya Anjaria
(74) *Attorney, Agent, or Firm* — Bell & Manning, LLC

(57) ABSTRACT

A system for treating atrial fibrillation includes a memory configured to store a baseline measurement of an atrial fibrillation characteristic of a patient and a post administration measurement of the atrial fibrillation characteristic of the patient. The post administration measurement is obtained subsequent to administration of a reactive oxygens species (ROS) scavenger to the patient. The system also includes a processor operatively coupled to the memory and configured to determine a change between the baseline measurement and the post administration measurement of the atrial fibrillation characteristic. The processor is further configured to identify, based on the determined change, one or more hot spots of atrial fibrillation, where the one or more hot spots comprise target areas for treatment of the atrial fibrillation.

18 Claims, 25 Drawing Sheets

Related U.S. Application Data on Jun. 17, 2020, provisional application No. 63/020,224, filed on May 5, 2020.

(51) Int. Cl.
| | |
|---|---|
| *A61B 5/339* | (2021.01) |
| *G16H 50/20* | (2018.01) |
| *A61K 31/198* | (2006.01) |
| *G16H 50/30* | (2018.01) |

(56) References Cited

U.S. PATENT DOCUMENTS

| | | | |
|---|---|---|---|
| 2015/0216435 A1* | 8/2015 | Bokan | A61N 1/3629 600/509 |
| 2017/0172440 A1* | 6/2017 | Arora | A61B 18/1492 |
| 2017/0296055 A1 | 10/2017 | Gardner et al. | |
| 2018/0055813 A1* | 3/2018 | Kurz | A61K 31/343 |
| 2018/0103865 A1 | 4/2018 | Trayanova et al. | |
| 2018/0296111 A1 | 10/2018 | Deno et al. | |
| 2019/0008405 A1 | 1/2019 | Bunch et al. | |
| 2019/0275339 A1 | 9/2019 | Ghosh et al. | |
| 2020/0196891 A1 | 6/2020 | Timofeyev et al. | |

OTHER PUBLICATIONS

GV Naccarelli et al., "Increasing prevalence of atrial fibrillation and flutter in the United States," *Am J Cardiol.* 2009, vol. 104; pp. 1534-1539.

JM Wiener et al., "Population ageing in the United States of America: implications for public programmes," *Int J Epidemiol.* 2002, vol. 31; pp. 776-781.

EJ Benjamin et al., "Impact of atrial fibrillation on the risk of death: the Framingham Heart Study," *Circulation.* 1998, vol. 98; pp. 946-952.

Ji-Youn Youn et al., "Oxidative stress in atrial fibrillation: an emerging role of NADPH oxidase," *J Mol Cell Cardiol.* 2013, vol. 62; pp. 72-79.

Claudio Ceconi et al., "Oxidative stress in cardiovascular disease: myth or fact?" *Archives of Biochemistry and Biophysics.* 2003, vol. 420; pp. 217-221.

H. Otani, "Oxidative Stress as Pathogenesis of Cardiovascular Risk Associated with Metabolic Syndrome," *Antioxid Redox Sign.* 2011, vol. 15, No. 7; pp. 1911-1926.

Michael P. Murphy, "How mitochondria produce reactive oxygen species," *Biochemical Journal.* 2009, vol. 417; pp. 1-13.

Ramon Rodrigo, "Prevention of postoperative atrial fibrillation: novel and safe strategy based on the modulation of the antioxidant system," *Front Physiol.* Apr. 12, 2012, vol. 3, Article 93; pp. 1-17.

Collin E. Murdoch et al., "NADPH oxidase-dependent redox signalling in cardiac hypertrophy, remodelling and failure," *Cardiovasc Res.* 2006; vol. 71; pp. 208-215.

Allison C. Cave et al, "NADPH oxidases in cardiovascular health and disease," *Antioxid Redox Signal.* 2006, vol. 8, Nos. 5 and 6; pp. 691-728.

M. Hori et al., "Oxidative stress and left ventricular remodelling after myocardial infarction," *Cardiovasc Res.* 2009, vol. 81; pp. 457-464.

Aaron. Kunamalla et al., "Constitutive Expression of a Dominant-Negative TGF-beta Type II Receptor in the Posterior Left Atrium Leads to Beneficial Remodeling of Atrial Fibrillation Substrate," *Circulation Research.* Jun. 24, 2016, ; vol. 119; pp. 69-82.

David J. Kennedy et al., "Central role for the cardiotonic steroid marinobufagenin in the pathogenesis of experimental uremic cardiomyopathy," *Hypertension.* 2006, vol. 47; pp. 488-495.

Maqsood M. Elahi et al., "Tracing the origins of postoperative atrial fibrillation: the concept of oxidative stress-mediated myocardial injury phenomenon," *Eur J Cardiov Prev R.* 2008, vol. 15, No. 6; pp. 735-741.

E. Babusikova et al., "Oxidative modification of rat cardiac mitochondrial membranes and myofibrils by hydroxyl radicals," *Gen Physiol Biophys.* 2004, vol. 23; pp. 327-335.

Michael J. Mihm et al., "Impaired myofibrillar energetics and oxidative injury during human atrial fibrillation," *Circulation.* 2001, vol. 104; pp. 174-180.

Mehmet Ozaydin et al., "N-acetylcysteine for the prevention of postoperative atrial fibrillation: a prospective, randomized, placebo-controlled pilot study: reply," *European Heart Journal.* 2008, vol. 29; pp. 1591-1591.

Hemantha Koduri et al., "Contribution of Fibrosis and the Autonomic Nervous System to Atrial Fibrillation Electrograms in Heart Failure," *Circ-Arrhythmia Elec.* 2012, vol. 5; pp. 640-649.

Koonlawee Nademanee et al., "A new approach for catheter ablation of atrial fibrillation: Mapping of the electrophysiologic substrate," *Journal of the American College of Cardiology.* 2004, vol. 43, No. 11; pp. 2044-2053.

Mark J. Shen et al., "Atrial Myopathy," *JACC Basic Transl Sci.* 2019, vol. 4, No. 5; pp. 640-654.

SM Narayan et al., "Treatment of Atrial Fibrillation by the Ablation of Localized Sources: CONFIRM (Conventional Ablation for Atrial Fibrillation With or Without Focal Impulse and Rotor Modulation) Trial," *J Am Coll Cardiol.* 2012, vol. 60, No. 7; pp. 628-636.

The Non-Final Office Action dated Jun. 27, 2023 for U.S. Appl. No. 17/521,545; pp. 1-13.

\* cited by examiner

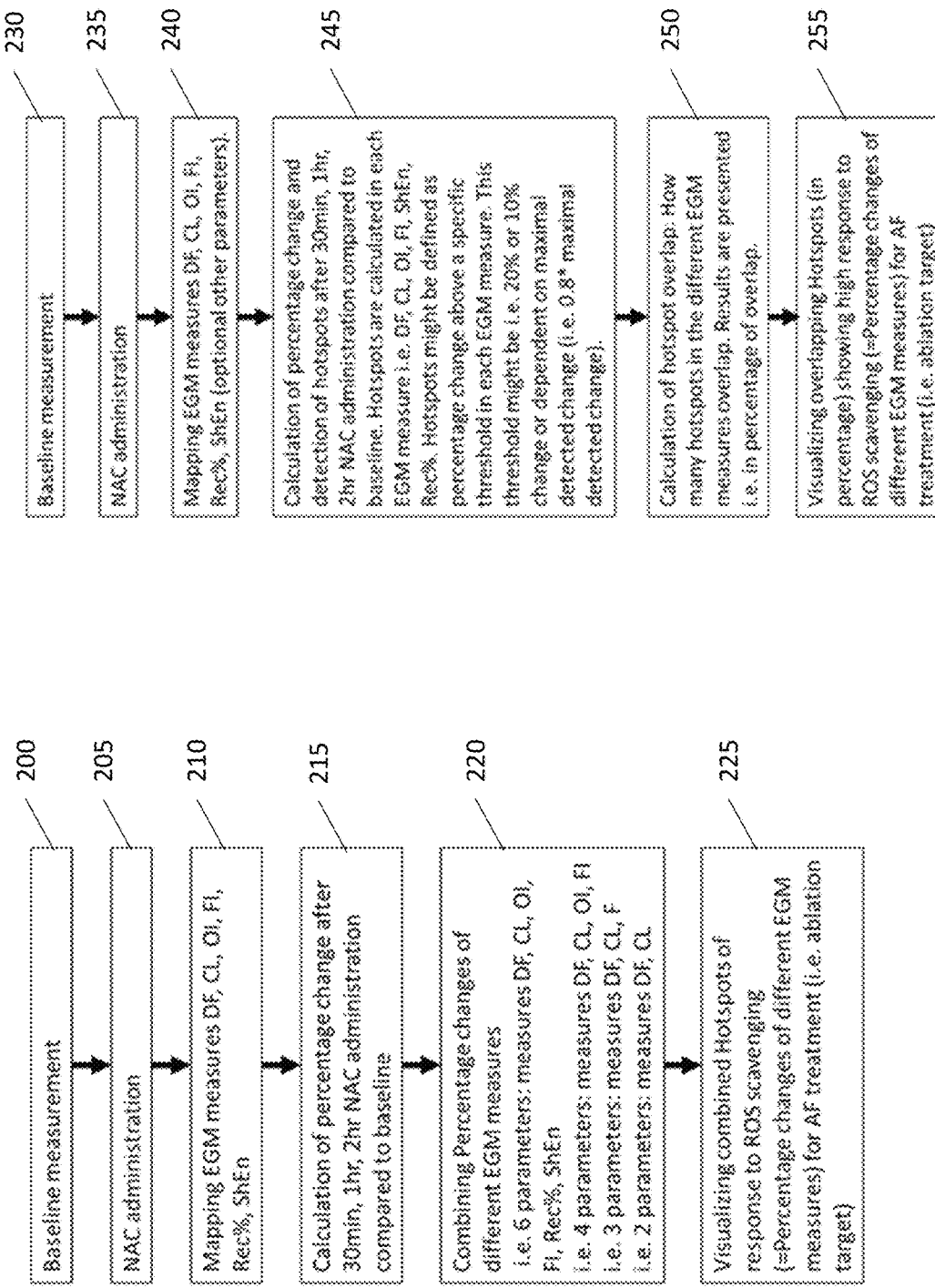

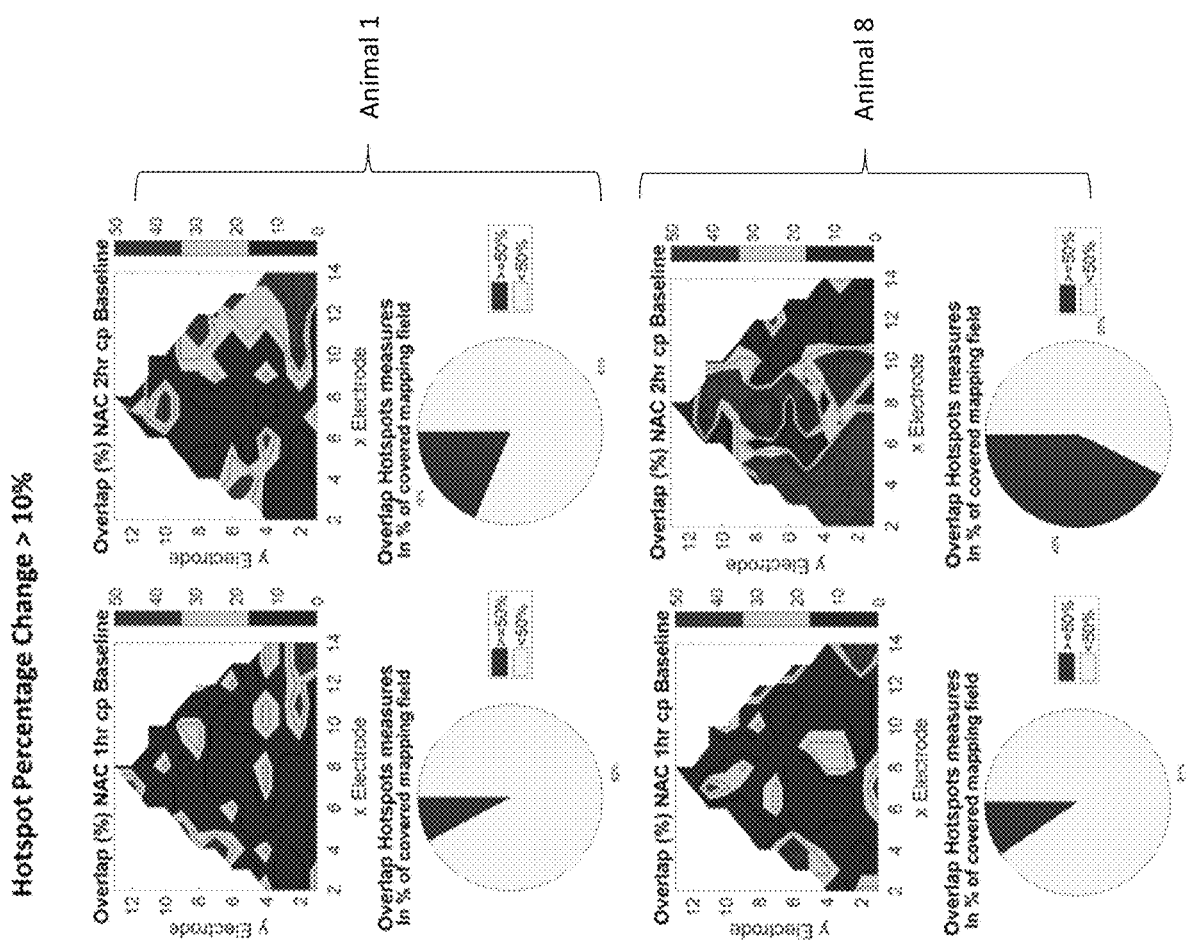

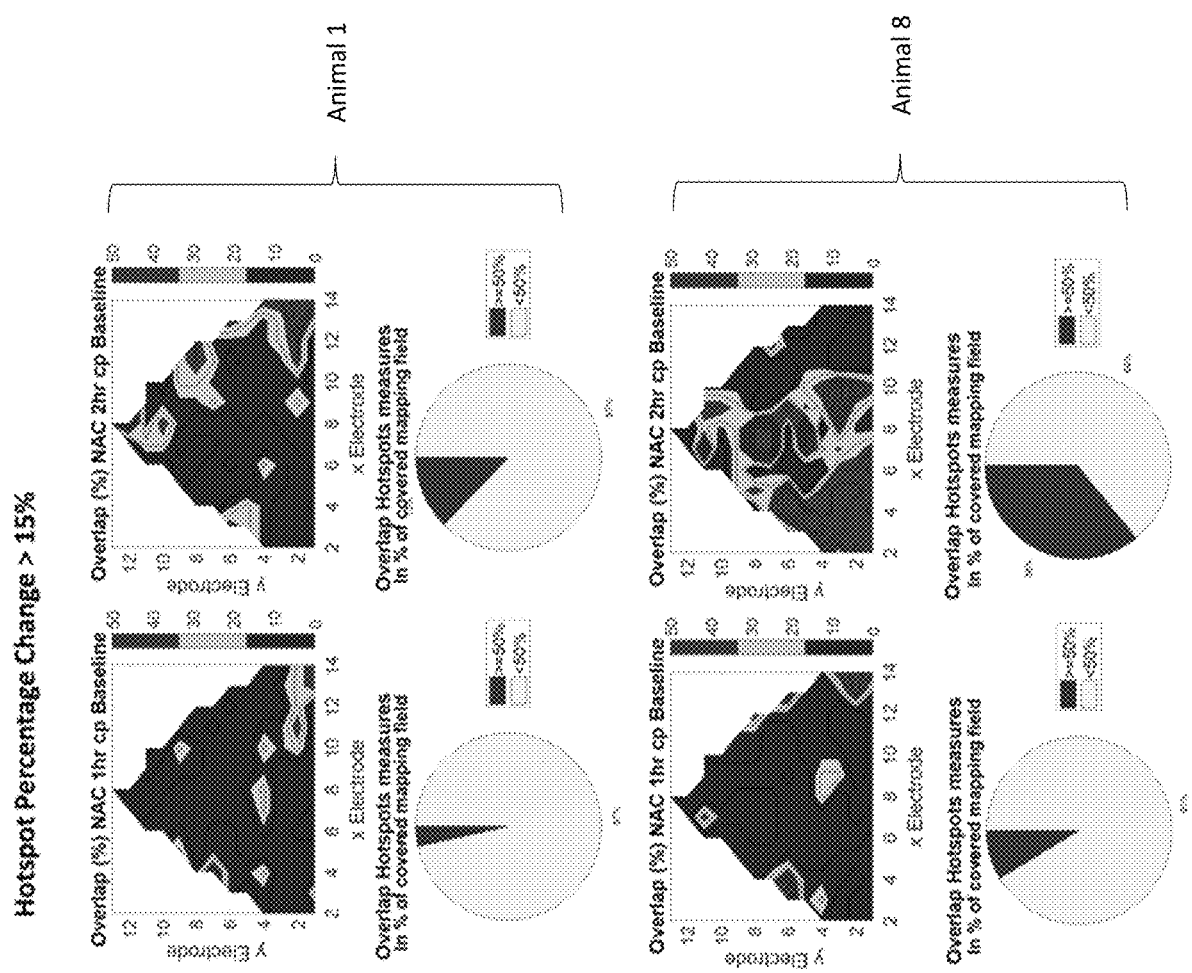

SYSTEM AND METHOD TO DETECT AND TREAT ARRHYTHMOGENIC REGIONS IN ATRIAL FIBRILLATION

CROSS-REFERENCE TO RELATED APPLICATIONS

The present application claims the priority benefit of U.S. Provisional App. No. 63/020,224 filed on May 5, 2020, U.S. Provisional App. No. 63/040,244 filed on Jun. 17, 2020, and U.S. Provisional App. No. 63/111,282 filed on Nov. 9, 2020, the entire disclosures of which are incorporated by reference herein.

REFERENCE TO GOVERNMENT RIGHTS

This invention was made with government support under HL125881 awarded by The National Institutes of Health (NIH). The government has certain rights in the invention.

BACKGROUND

Atrial fibrillation (AF) refers to a quivering or irregular heartbeat that can cause immediate symptoms such as heart palpitations, chest pain, fatigue, shortness of breath, dizziness, and overall weakness. Atrial fibrillation can also result in various long term health issues such as blood clots, heart failure, stroke, etc. During atrial fibrillation, the atrial (upper) chambers of the heart beat irregularly, which prevents normal blood flow through the (lower) ventricles.

SUMMARY

An illustrative system for treating atrial fibrillation includes a memory configured to store a baseline measurement of an atrial fibrillation characteristic of a patient and a post administration measurement of the atrial fibrillation characteristic of the patient. The post administration measurement is obtained subsequent to administration of a reactive oxygens species (ROS) scavenger to the patient. The system also includes a processor operatively coupled to the memory and configured to determine a change between the baseline measurement and the post administration measurement of the atrial fibrillation characteristic. The processor is further configured to identify, based on the determined change, one or more hot spots of atrial fibrillation, where the one or more hot spots comprise target areas for treatment of the atrial fibrillation.

An illustrative method of treating atrial fibrillation includes storing, in a memory of a computing system, a baseline measurement of an atrial fibrillation characteristic of a patient and a post administration measurement of the atrial fibrillation characteristic of the patient. The post administration measurement is obtained subsequent to administration of a reactive oxygens species (ROS) scavenger to the patient. The method also includes determining, by a processor operatively coupled to the memory, a change between the baseline measurement and the post administration measurement of the atrial fibrillation characteristic. The method further includes identifying, by the processor and based on the determined change, one or more hot spots of atrial fibrillation. The one or more hot spots comprise target areas for treatment of the atrial fibrillation.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 2A depicts an algorithm to determine percentage changes of electrogram measurements in accordance with an illustrative embodiment.

FIG. 2B depicts an algorithm to calculate overlapping hotspot regions of multiple electrogram measurements in accordance with an illustrative embodiment.

FIG. 5F shows hotspot overlap with hotspots defined as a percentage change of 10% at 1 hour and 2 hours after administration of the ROS scavenger in accordance with an illustrative embodiment.

FIG. 5G shows hotspot overlap with hotspots defined as a percentage change of 15% at 1 hour and 2 hours after administration of the ROS scavenger in accordance with an illustrative embodiment.

DETAILED DESCRIPTION

Figure 1A:
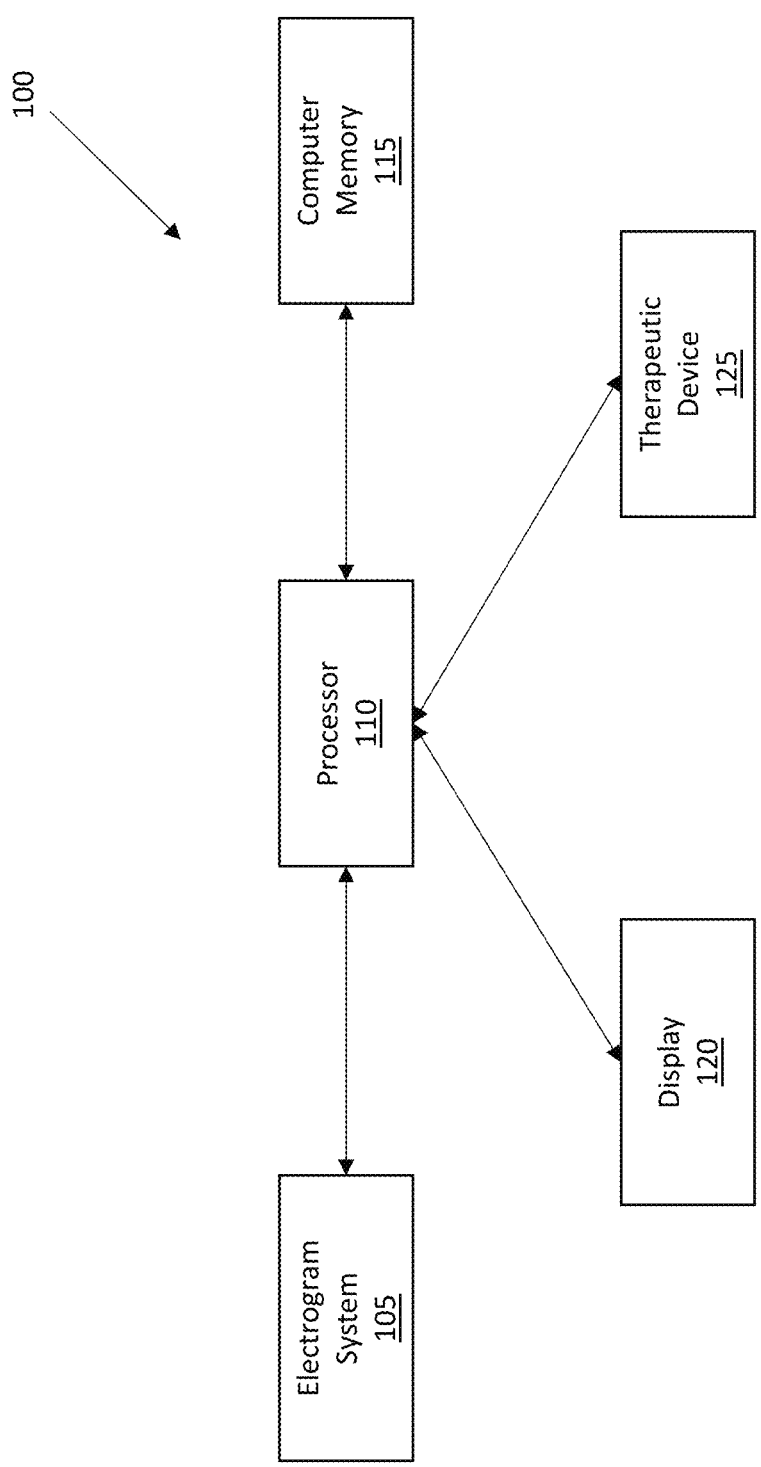
FIG. 1A depicts a system to detect and treat atrial fibrillation in accordance with an illustrative embodiment.

Atrial fibrillation (AF) is the most common form of heart arrhythmia, and it is estimated to currently affect more than 3 million people in the United States alone. By the year 2050, it is estimated that 1 in 5 Americans over the age of 65 (~7.6 million individuals) is expected to suffer from AF. Atrial Fibrillation is a serious condition that leads to a 1.9-fold increased risk of mortality, and a 5-fold higher risk of stroke. Additionally, heart disease costs the United States about $219 billion each year. Based on prevalence, death rates, disability, and cost, cardiovascular diseases will likely continue to be the most burdensome disease that Americans will face in the coming decades.

Unfortunately, antiarrhythmic drugs and catheter ablation therapies (e.g., PVI, OI, FI, ShEn, CFAE, DF, etc.) have limited efficacy in the treatment of atrial fibrillation, likely because they are not targeting the underlying molecular and structural mechanisms of AF. Thus, new systems and software algorithms are needed to optimize the clinical procedures used to treat AF. Described herein are novel systems and methods/algorithms for the detection of oxidative stress levels by detecting hotspot sub-regions of high reactive oxygen species scavenger responses in electrograms.

Oxidative Stress (OS) is an important mechanism underlying atrial fibrillation (AF). However, traditional clinical procedures and electrophysiological studies do not take the OS level in different heart regions into consideration when treating AF. The proposed methods and systems detect OS using multiple electrogram measures at baseline after a reactive oxygen species (ROS) scavenger (e.g., N-acetyl-cysteine (NAC)) is administered to identify hotspot regions which show strong responses of intracardiac signal recording. The hotspot regions represent treatment targets for ablation or gene therapy. The ROS scavenger N-acetylcysteine is an antioxidant, and is listed on the World Health Organization (WHO) Model List of Essential Medicines. In alternative embodiments, a different type of ROS scavenger may be used. The proposed methods and systems also target the underlying molecular and structural mechanisms of AF. Further, responses and changes in activation patterns like rotational activity, focal activity, and wavelet activity are quantified before and after application of the ROS scavenger, and are used to guide the AF treatment target points.

In developing the proposed system, a variety of methods were used to detect pro-arrhythmogenic regions based on intracardiac signal recording during AF. Initially, it was thought that regions showing complex fractionated electrograms (CFAE) might correlate with vulnerable substrate (e.g., fibrosis, autonomic nerves) and were proposed for the identification of AF sources and as ablation target points. However, use of the CFAE data did not result in a beneficial correlation. The inventors subsequently derived an entirely new explanation and treatment for targeting molecular mechanisms of AF using AF characteristics. Specifically, algorithms were developed and used to automatically detect the effect of oxidative stress on the pathophysiological substrate, based on electrograms. This new method shows a strong relationship of AF characteristics measured with EGMs and the oxidative stress level. This new method also automatically identifies regions of oxidative injury. This novel automatic detection algorithm can be integrated into clinical navigation systems to display hotspot regions and AF characteristics to physicians after administration of antioxidants (e.g., NAC). The proposed methods can also be used to develop local activation time and/or voltage maps for future ablation or gene therapy target points and optimized clinical treatments.

In an illustrative embodiment, the proposed method and system involve use of an electrogram to monitor a patient's heart characteristics. An electrode recording system can be used to receive and store baseline electrogram signals from the heart of the patient during sinus rhythm. As discussed in more detail below, mapping is performed based on the received electrogram signals to generate high resolution maps in multiple atrial regions of the patient. A reactive oxygen species scavenger (e.g., NAC) is then administered to the patient. The electrogram is used to measure various characteristics of the heart after administration of the ROS scavenger. These characteristics can include dominant frequency (DF), cycle length (CL), organization index (OI), fractionation index (FI), recurrence morphology percentage (Rec %), Shannon's entropy (ShEn), conduction velocity, and voltage. The monitored characteristics can also include the number and stability of rotational, focal, and wavelet activities in different atrial regions of the heart. The various atrial regions of the heart can include posterior left atrium (PLA), left atrial free wall (LAFW), left atrial appendage (LAA), posterior right atrium (PRA), right atrial free wall (RAFW), right atrial appendage (RAA), etc. In alternative embodiments, different heart regions may be used.

In an illustrative embodiment, the proposed system uses a computing system to perform calculation of percentage changes of AF characteristics at each electrogram electrode location at different time intervals subsequent to administration of the ROS scavenger. The percentage changes are based on the baseline readings from the electrogram (i.e., the readings received prior to administration of the ROS scavenger). For example, the calculations of percentage changes can be after 30 minutes, 1 hour, and 2 hours in one embodiment. Alternatively, different or additional times may be used, such as 45 minutes, 1.5 hours, 3 hours, 4 hours, etc. In some implementations, rebolus of the ROS scavenger administration may be performed in between the time periods.

The computing system is used to combine the percentage changes of different EGM measures in an effort to identify hotspot regions of AF in the heart. The percentage changes can be based on any number of parameters, such as 6 parameters (e.g., measures of DF, CL, OI, FI, Rec %, ShEn), 4 parameters (e.g., measures of DF, CL, OI, FI), 3 parameters (e.g., measures of DF, CL, FI), 2 parameters (e.g., measures of DF, CL), etc. In alternative embodiments, different numbers of characteristics and/or different characteristics may be combined. The percentage changes can also be based on the number and stability of rotational, focal, and wavelet activities in different atrial regions before and after ROS scavenger administration. Based on these percentage changes, the system can calculate overlapping hotspot regions based on single EGM measurements, the combination of multiple EGM measurements, multivariate changes of EGM measures, and activation pattern (i.e., number of rotational, focal, and wavelet activities, and their frequency and stability over time) before and after administration.

The computing system can also generate a visualization of hotspots that are identified based on the percentage changes that occur due to the ROS scavenging. Once the hotspots are identified, these hotspots can be designated for AF treatment such as ablation or gene therapy. For example, in one embodiment, ablation can be performed on the hotspots (i.e., the areas that exhibited strong responses to the ROS scavenging) in an effort to alleviate the AF. Subsequent to performing the ablation (or other treatment), the system can repeat the process of ROS scavenger administration, electrogram monitoring, determination of percentage changes, determination of hotspot regions, and visualization to determine the effectiveness of the treatment and to determine the best approach for subsequent treatments.

For example, the system can obtain electrogram readings and remap the atrial regions of the heart. The system can also administer the ROS scavenger, take readings over a period of time, determine percentage changes, and combine the percentage changes of the different EGM measurements based on various combinations of the monitored characteristics such as measurements of DF, CL, OI, FI, Rec %, ShEn, measurements of DF, CL, OI, FI, measures of DF, CL, FI, measurements of DF, CL, etc. Based on these percentage changes, the system can calculate overlapping hotspot regions of multiple EGM measures, multivariate changes of EGM measures, and activation pattern (i.e., number of rotational, focal, and wavelet activities, and their frequency and stability over time) before and after ROS scavenger administration. The computing system can also generate a visualization of hotspots that are identified based on the percentage changes that occur due to the ROS scavenging. Once the hotspots are identified, these hotspots can be designated for further AF treatment. This process can be repeated until the AF is terminated.

The above-described algorithms and the system used to perform the algorithms are described in more detail with reference to the figures. FIG. 1A depicts a system 100 to detect and treat atrial fibrillation in accordance with an illustrative embodiment. As shown, the system 100 includes an electrogram system 105 that is used to obtain heart readings through a plurality of electrogram electrodes as known in the art. The electrogram system 105 is in wired or wireless communication with a computing device that includes a processor 110, a computer memory 115, and a display 120. In alternative embodiments, the computing device can include additional or different components such as a transceiver (transmitter and/or receiver), power source, user interface (keyboard, mouse, touchscreen, etc.), etc. In some embodiments, the electrogram system 105 includes or is connected to an imaging system such that a user is able to perform directed navigation to identified hotspots and other regions of interest. The imaging system can be a magnetic resonance imaging (MRI) system, an x-ray system, an ultrasound system, etc.

Also in communication with the computing device is a therapeutic device 125 that is used to administer the ROS scavenger to the patient and/or perform treatment on identified hotspot areas. The therapeutic device 125 can include an intravenous (IV) tube attached to the patient and designed to deliver therapeutic substances to the patient from a reservoir attached to the IV tube. In an illustrative embodiment, the computing device can be used to perform any of the calculations and other operations described herein. Specifically, the algorithms, software, and operations described herein can be stored in the computer memory 115 as computer-readable instructions. Upon execution of the computer-readable instructions by the processor 110, the computing device performs the operations.

Figure 1C:
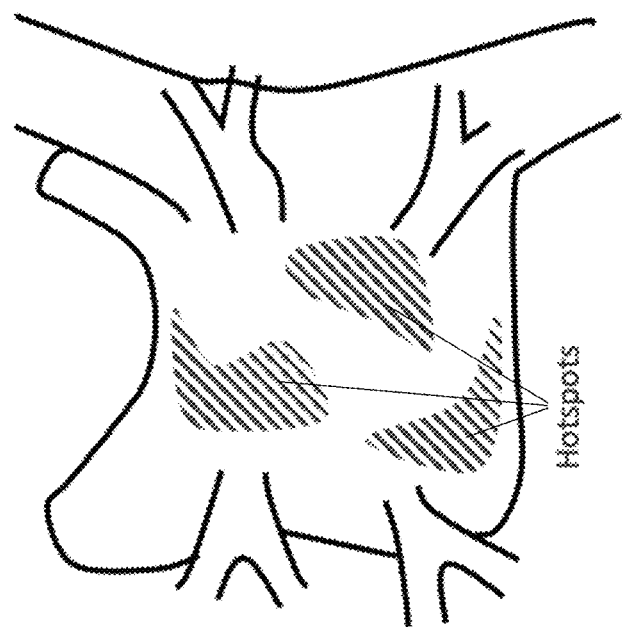
FIG. 1C is a schematic illustration of hotspots of atrial fibrillation characteristic changes in the atrium in accordance with an illustrative embodiment.
Figure 1B:
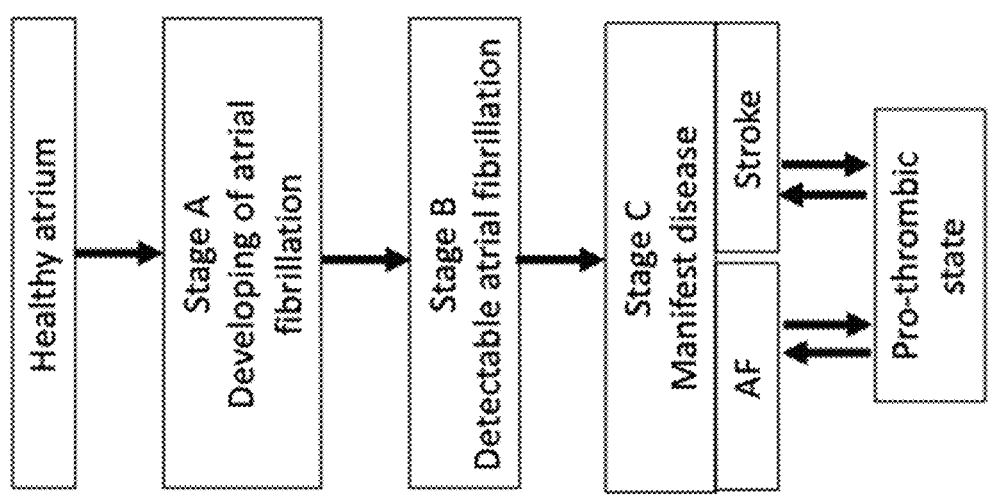
FIG. 1B is a schematic illustration of potential mechanisms of oxidative stress on atrial fibrillation in accordance with an illustrative embodiment.

FIG. 1B is a schematic illustration of potential mechanisms of oxidative stress on atrial fibrillation in accordance with an illustrative embodiment. As shown, AF typically develops in several steps until it becomes manifest, including continued electrical, structural, and autonomic remodeling. Specifically, a healthy atrium may be exposed to oxidative stress, inflammation, and simple aging, any of which can result in Stage A, which is the initial development of atrial fibrillation. As a result of electrophysiological remodeling, structural remodeling, autonomic remodeling, fibrosis, etc., Stage B may be reached, at which point the atrial fibrillation is detectable. As a result of continued remodeling, stage C is reached in which the disease is manifest. Atrial fibrosis and/or inflammation can result in a pro-thrombic state, which may result in stroke, increased atrial fibrillation, thrombosis, etc.

FIG. 1C is a schematic illustration of hotspots of atrial fibrillation characteristic changes in the atrium in accordance with an illustrative embodiment. In one embodiment, these identified hotspots can be displayed such that a physician is able to perform a targeted treatment. The hotspots can be presented on a computer display, and in some embodiments an imaging system (x-ray, magnetic resonance imaging, etc.) or other navigation system can be used to assist the physician in targeting the specific hotspot regions of interest with ablation, gene therapy, etc.

Figure 2C:
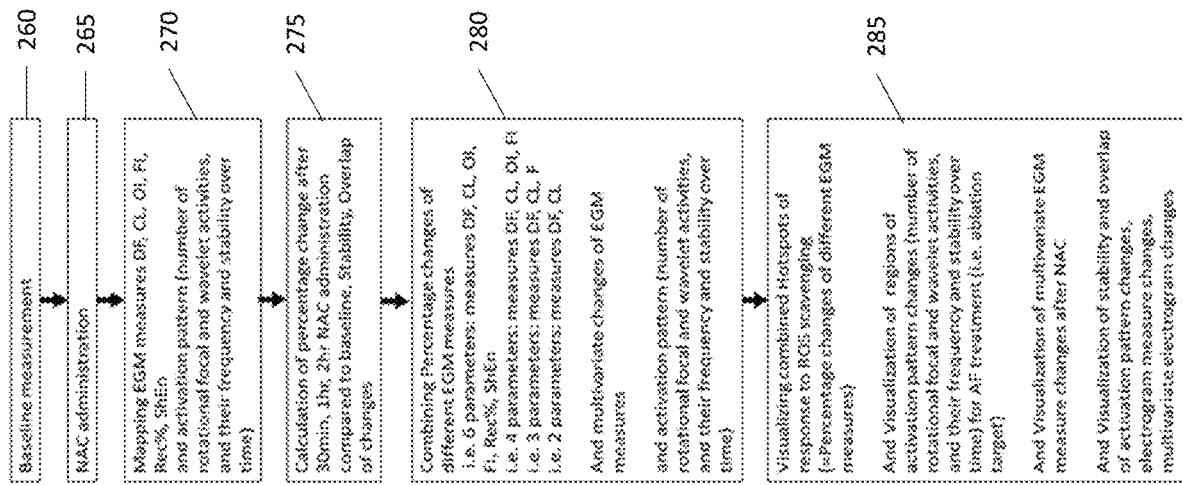
FIG. 2C depicts an algorithm to calculate overlapping hotspot regions and percentage change of multiple electrogram measurements and overlapping regions showing reduced atrial fibrillation sources in accordance with an illustrative embodiment.

FIGS. 2A-2C are flow charts depicting algorithm workflows for detecting oxidative stress hotspot regions in a heart. In alternative embodiments, fewer, additional, and/or different operations may be performed. Also, the use of flow diagrams is not meant to be limiting with respect to the order of operations performed. FIG. 2A depicts an algorithm to determine percentage changes of electrogram measurements in accordance with an illustrative embodiment. FIG. 2B depicts an algorithm to calculate overlapping hotspot regions of multiple electrogram measurements in accordance with an illustrative embodiment. FIG. 2C depicts an algorithm to calculate overlapping hotspot regions and percentage change of multiple electrogram measurements and overlapping regions showing reduced atrial fibrillation sources in accordance with an illustrative embodiment.

Referring to FIG. 2A, a baseline measurement for each of a plurality of characteristics is obtained using an electrogram in an operation 200. The baseline measurements are measured prior to administration of the ROS scavenger. The ROS scavenger is administered in an operation 205, and mapping of the various characteristics is performed based on electrogram measured characteristics in an operation 210. The characteristics measured by the electrogram system can include DF, CL, OI, FI, Rec %, ShEn, etc. The system continues conducting measurements using the electrogram at various periods of time subsequent to administration of the ROS scavenger, such as 30 minutes, 1 hour, 2 hours, etc. Alternatively, different periods of time may be used. The system also calculates the percentage change for each of the measured characteristics at each of the periods of time, as compared to the baseline measurements in an operation 215. The percentage changes of various measured characteristics are combined, as shown in an operation 220. In alternative embodiments, different combinations may be used and/or different numbers of characteristics may be combined, such as 5, 7, etc. The areas of the heart having the highest combined percentage changes are identified as hotspots, and the system maps these hotspots onto the heart so that they can be visualized in an operation 225. The hotspots are then targeted for treatment.

Referring to FIG. 2B, a baseline measurement for each of a plurality of characteristics is obtained using the electrogram system in an operation 230. The baseline measurements are measured prior to administration of the ROS scavenger in an operation 235, and mapping of the various characteristics is performed based on the measured characteristics in an operation 240. Any of the characteristics described herein can be used. The system continues conducting measurements using the electrogram at various periods of time subsequent to administration of the ROS scavenger, such as 30 minutes, 1 hour, 2 hours, etc. The system also calculates the percentage change for each of the measured characteristics at each of the periods of time, as compared to the baseline measurements in an operation 245. Hotspots are identified for each measured characteristic based on the percentage changes in the operation 245. In one embodiment, the determined percentage changes are compared to a percentage change threshold to determine whether a given area is a hotspot. The percentage change threshold can be 5%, 8%, 10%, 20%, etc. depending on the implementation. Alternatively, instead of basing the determination on the percentage change, the determination of whether an area is a hotspot can be based on the amount of absolute change in the measured characteristic, and can vary for each characteristic. Based on the identified hotspots, the system also calculates the percentage of overlap among the various hotspots from each of the characteristics in an operation 250. The system maps the overlapping hotspots (based on the percentage of overlap) so that they can be visualized in an operation 255, and the overlapping hotspots are then targeted for treatment.

Referring to FIG. 2C, similar to the aforementioned algorithms, a baseline measurement for each of a plurality of characteristics is obtained using the electrogram system in an operation 260. The baseline measurements are measured prior to administration of the ROS scavenger in an operation 265, and mapping of the various characteristics is performed based on the measured characteristics in an operation 270. Any of the characteristics described herein can be used. An activation pattern is also mapped, where the activation pattern refers to the number of rotational, focal, and wavelet activities, along with their frequency and stability over time.

The system continues conducting measurements using the electrogram at various periods of time subsequent to administration of the ROS scavenger, such as 30 minutes, 1 hour, 2 hours, etc. The system also calculates the percentage change for each of the measured characteristics at each of the periods of time, as compared to the baseline measurements, stability, and overlap of changes in an operation 275. The system combines percentage changes of the various measured characteristics, as shown in an operation 280. The system also determines multivariate changes of the electrogram measurements for the characteristics, and the activation pattern. The system identifies and maps the hotspots based on the combined percentages in an operation 285. The system also maps regions of activation pattern changes and multivariate changes of the measured characteristics after application of the ROS scavenger. The system further maps stability and overlap of the activation pattern changes, electrogram measurement changes of the characteristics, and the multivariate changes of the measured characteristics in the operation 285. The mappings are used to determine areas to target with the treatment, and also to determine the effectiveness of prior treatments and to make determinations regarding subsequent treatments.

Figure 3A:
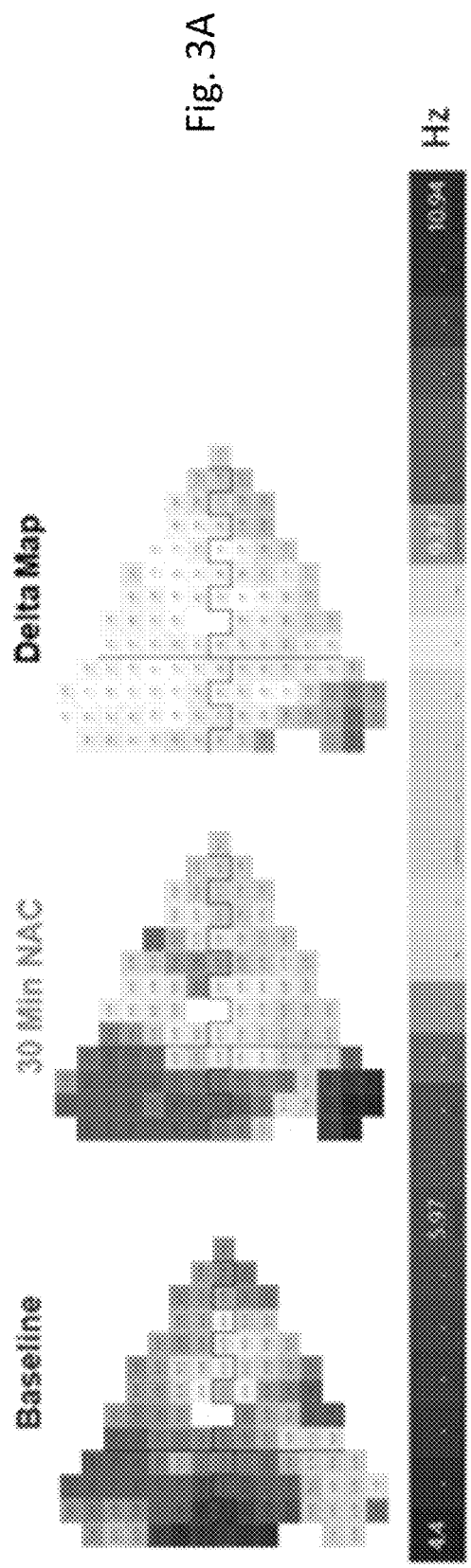
FIG. 3A depicts mapping plaques based on open chest epicardial electrogram mapping of atrial fibrillation in accordance with an illustrative embodiment.
Figure 3B:
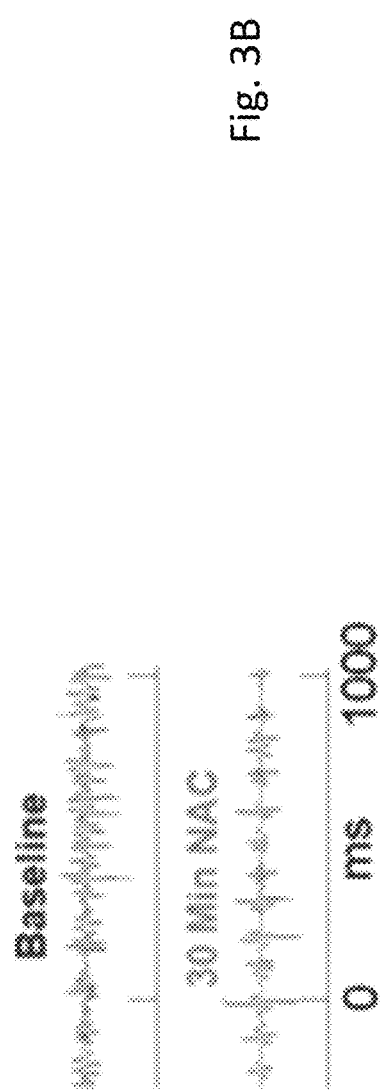
FIG. 3B depicts representative electrograms at baseline and 30 minutes after ROS scavenger administration in accordance with an illustrative embodiment.
Figure 3C:
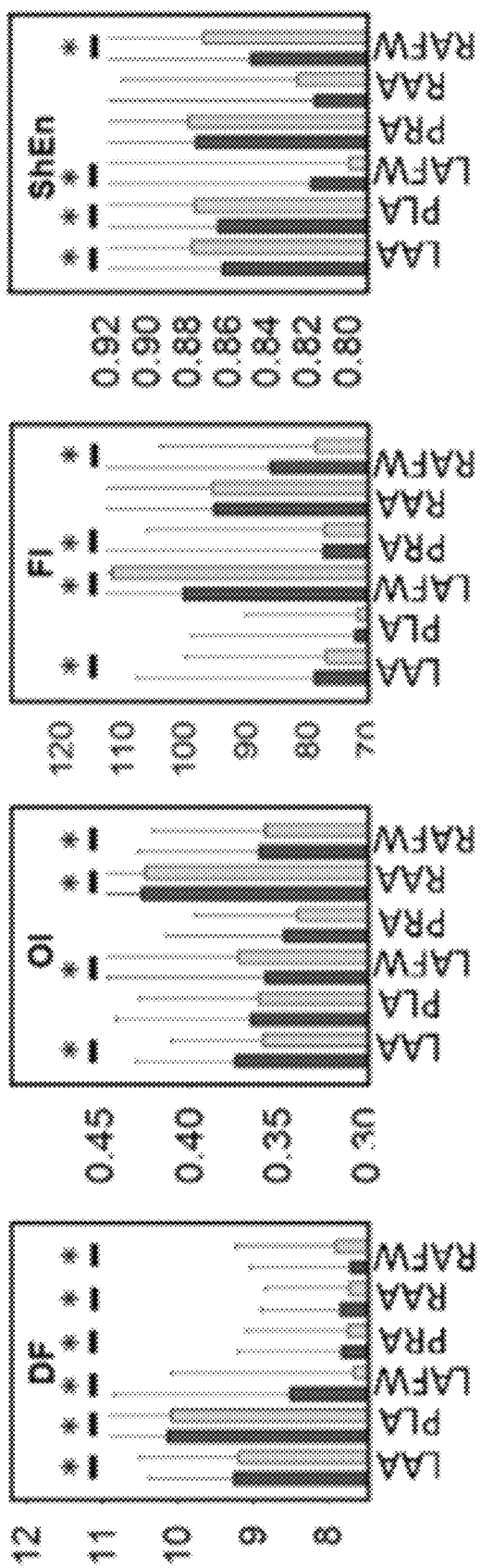
FIG. 3C depicts analysis of DF, OI, FI and ShEn characteristics in the LAA, LAFW, PLA, PRA, RAA, and RAFW regions of the heart in accordance with an illustrative embodiment.

Experiments were conducted on animals using the techniques described herein. FIGS. 3A-3C depict mapping of electrogram measured characteristics at baseline and 30 minutes after administration of an ROS scavenger during an experiment. Specifically, FIG. 3A depicts mapping plaques based on open chest epicardial electrogram mapping of atrial fibrillation in accordance with an illustrative embodiment. The electrogram used 117 electrodes and 2.5 mm interelectrode spacing. In alternative embodiments, a different number of electrodes and/or different spacing may be used. FIG. 3A shows a representative high-density map of dominant frequency at baseline (left), 30 minutes after ROS scavenger administration (middle), and the corresponding delta map (ROS scavenger-baseline). FIG. 3B depicts representative electrograms at baseline and 30 minutes after ROS scavenger administration in accordance with an illustrative embodiment. FIG. 3C depicts analysis of DF, OI, FI and ShEn in the LAA, LAFW, PLA, PRA, RAA, and RAFW regions of the heart in accordance with an illustrative embodiment.

Figure 4A:
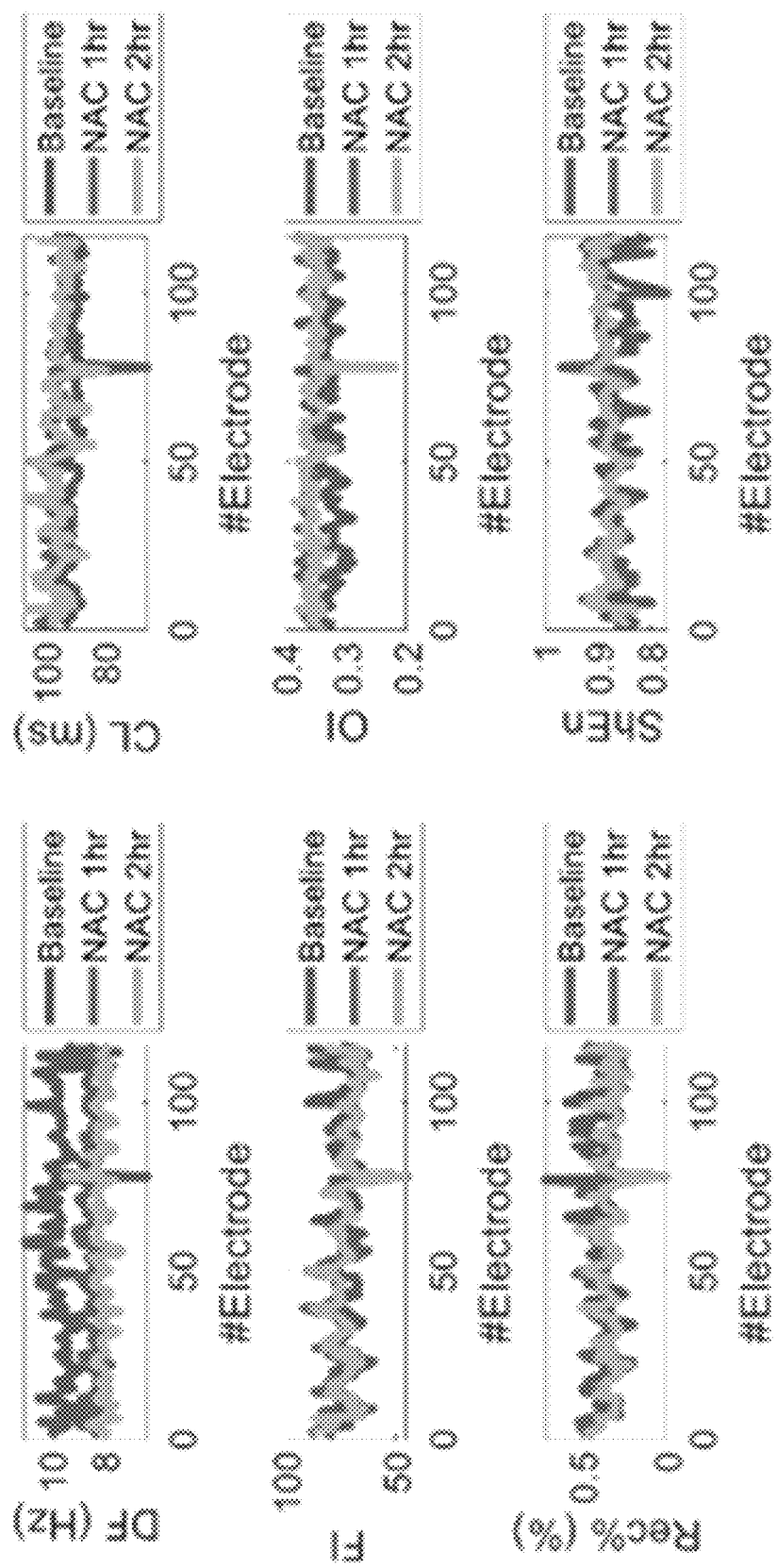
FIG. 4A depicts stepwise changes in measured characteristic values one hour and two hours after administration of the ROS scavenger as compared to a baseline measurement in accordance with an illustrative embodiment.
Figure 4B:
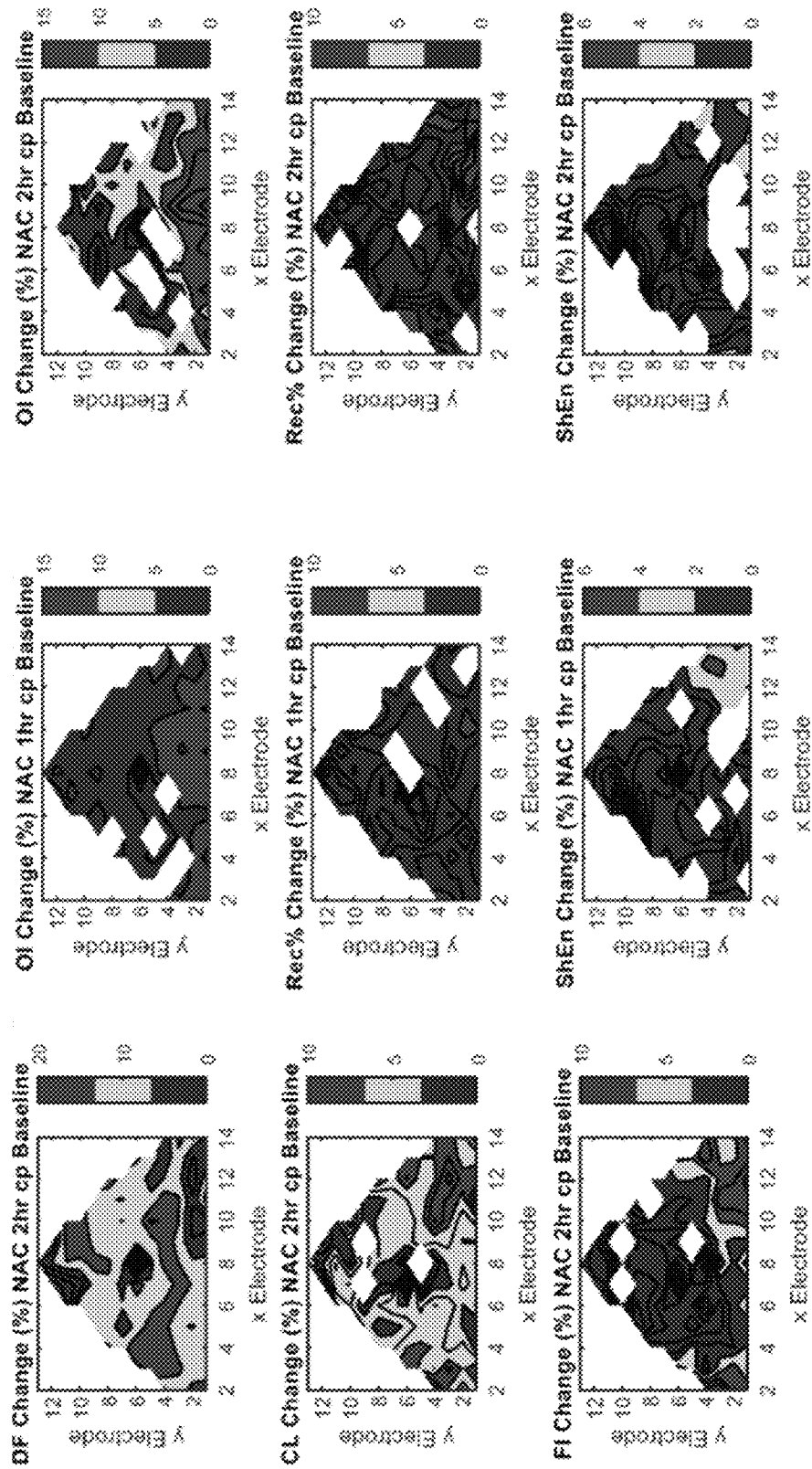
FIG. 4B depicts hotspots of AF characteristic changes in DF, OI, CL, Rec %, FI and ShEn in the LAFW region of the heart in accordance with an illustrative embodiment.
Figure 4C:
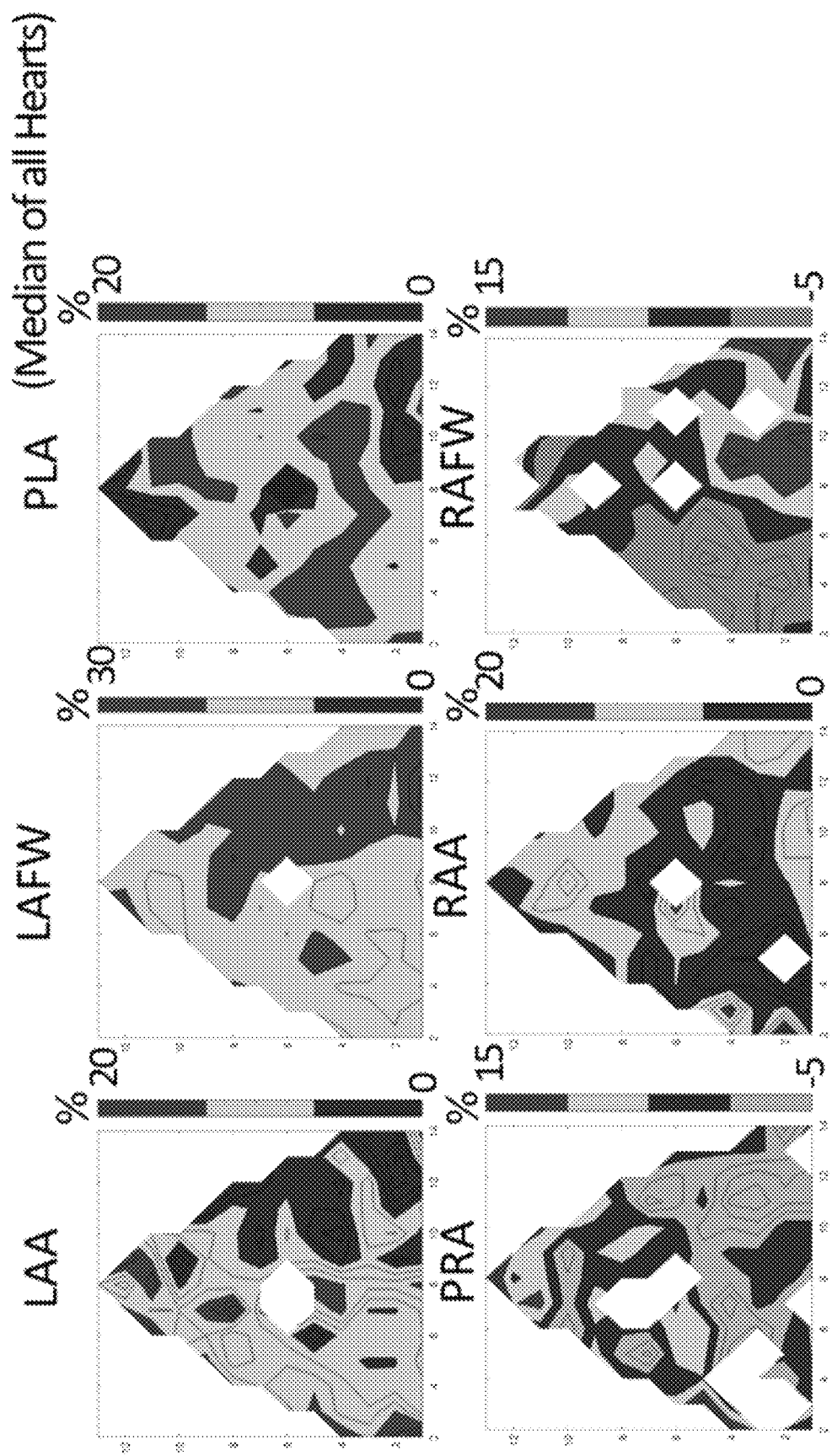
FIG. 4C depicts hotspots in six regions of the heart in accordance with an illustrative embodiment.
Figure 4D:
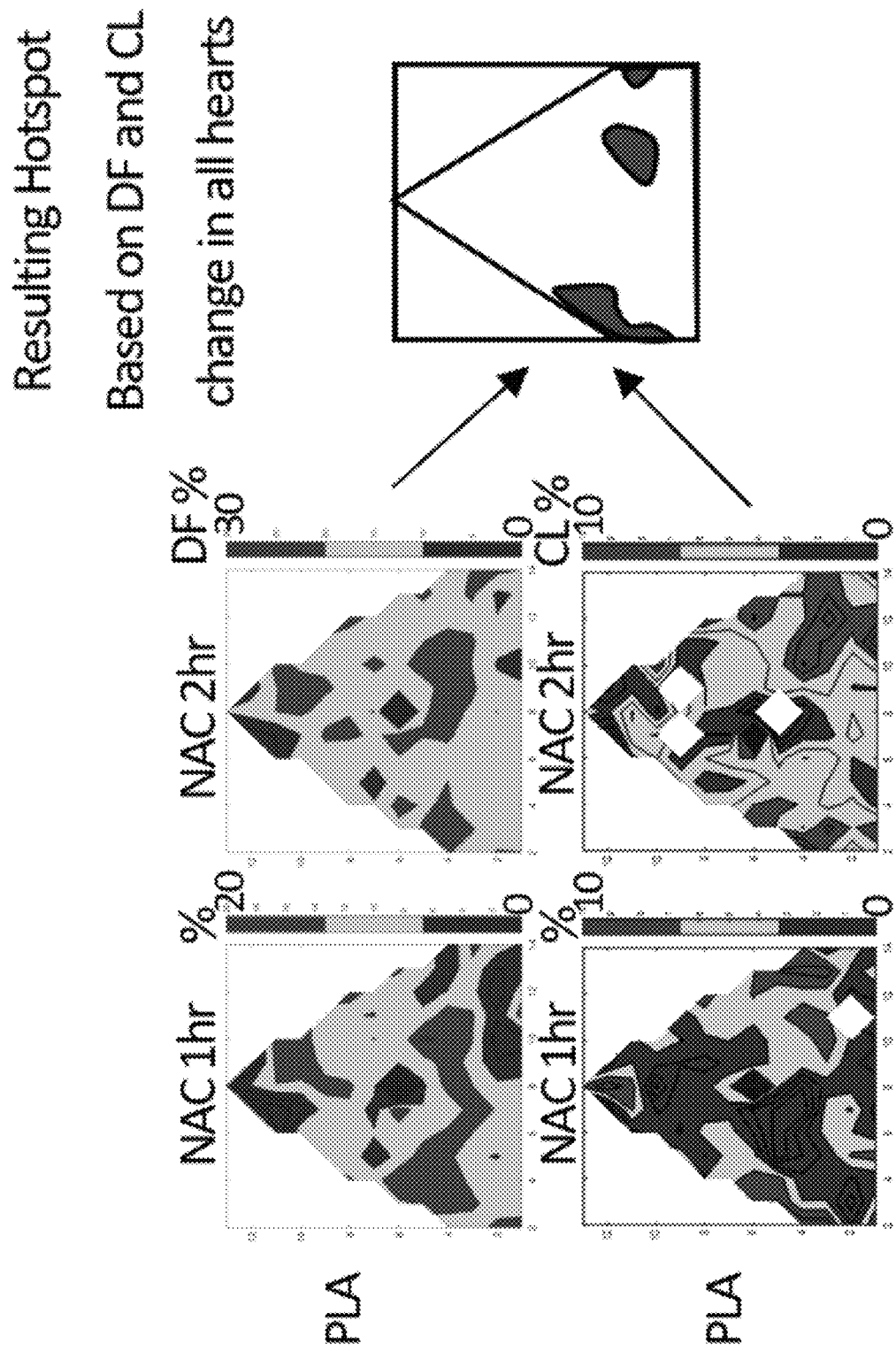
FIG. 4D depicts the overlap of hotspots based on DF and CL hotspots in accordance with an illustrative embodiment.

FIGS. 4A-4D demonstrate a strong beneficial change in median values for measured characteristics of 10 animals in each of 117 electrode locations in the LAFW. FIG. 4A depicts stepwise changes in measured characteristic values one hour and two hours after administration of the ROS scavenger as compared to baseline in accordance with an illustrative embodiment. FIG. 4B depicts hotspots of AF characteristic change in DF, OI, CL, Rec %, FI and ShEn in the LAFW region of the heart in accordance with an illustrative embodiment. FIG. 4C depicts hotspots in six regions of the heart in accordance with an illustrative embodiment. As shown, large hotspots regions were detected in the LAFW and PLA and there were beneficial changes in the right atrium. FIG. 4D depicts the overlap of hotspots based on DF and CL hotspots in accordance with an illustrative embodiment.

FIG. 5 depicts data obtained from the animal test subjects. FIG. 5A shows measurement values of 6 characteristics in all 117 electrodes in the LAFW region of the heart in accordance with an illustrative embodiment. FIG. 5B depicts combined hotspot analyses (left) and overlapping hotspots (right) showing how many hotspots of the six EGM measures overlap, presented in percentage of the six measured characteristics in accordance with an illustrative embodiment. FIG. 5C is a histogram of hotspot overlap in percentage of how many electrogram measures overlap at 1 hour and 2 hours in accordance with an illustrative embodiment. FIG. 5D is a pie chart of hotspot overlap with >50% change in accordance with an illustrative embodiment. As shown, 36% of the mapping field showed hotspot overlap in >50% of the EGM measures in Animal 1 at 1 h hour after ROS scavenger administration and 13% after 2 hours. In Animal 8, hotspot overlap in >50% of the EGM measures covered 15% and 48% of the mapping field in the LAFW at 1 hour and hours after administration.

Figure 5A:
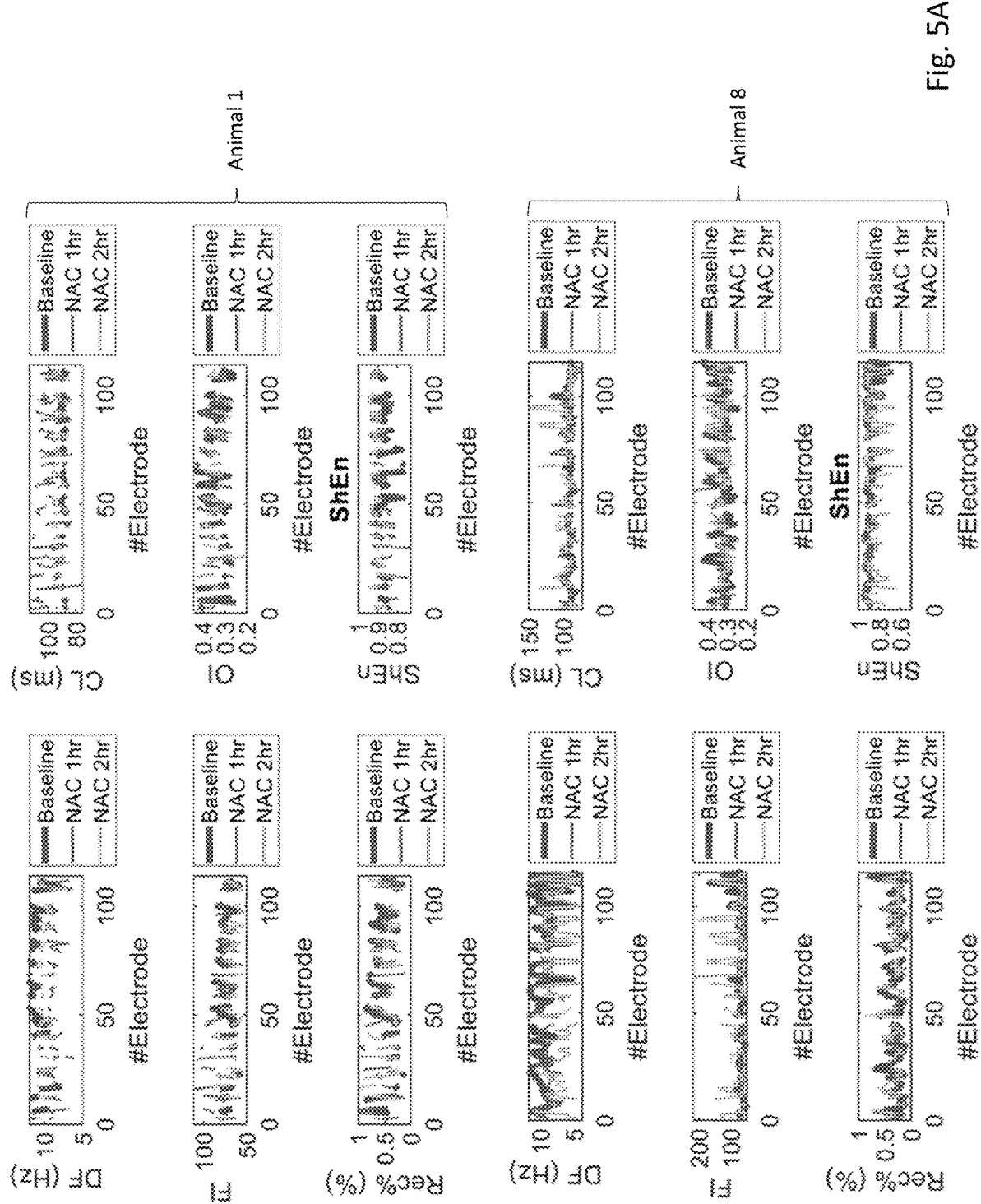
FIG. 5A shows measurement values of 6 characteristics in all 117 electrodes in the LAFW region of the heart in accordance with an illustrative embodiment.
Figure 5B:
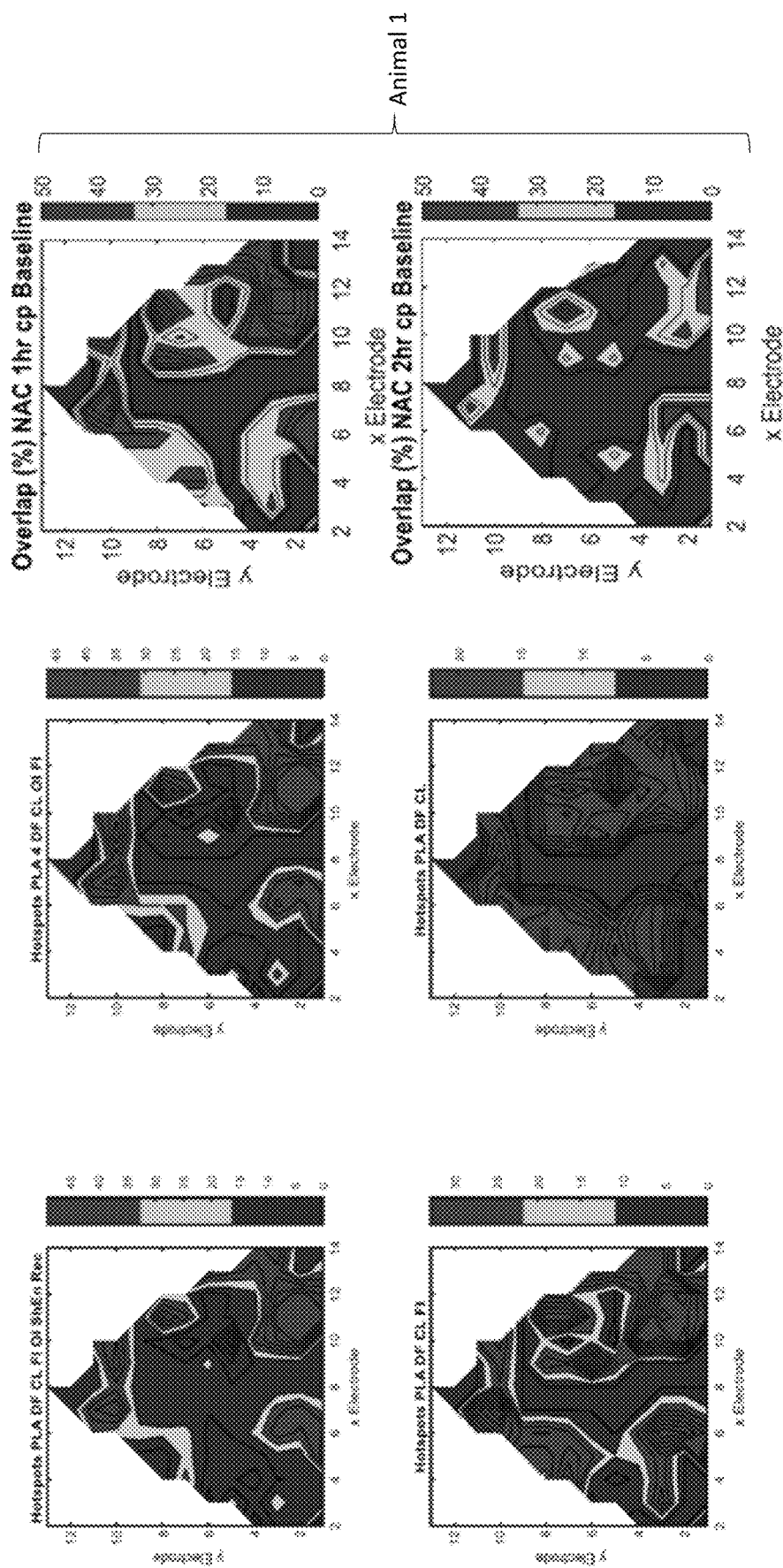
FIG. 5B depicts combined hotspot analyses (left) and overlapping hotspots (right) showing how many hotspots of the six EGM measures overlap, presented in percentage of the six measured characteristics in accordance with an illustrative embodiment.
Figure 5B:
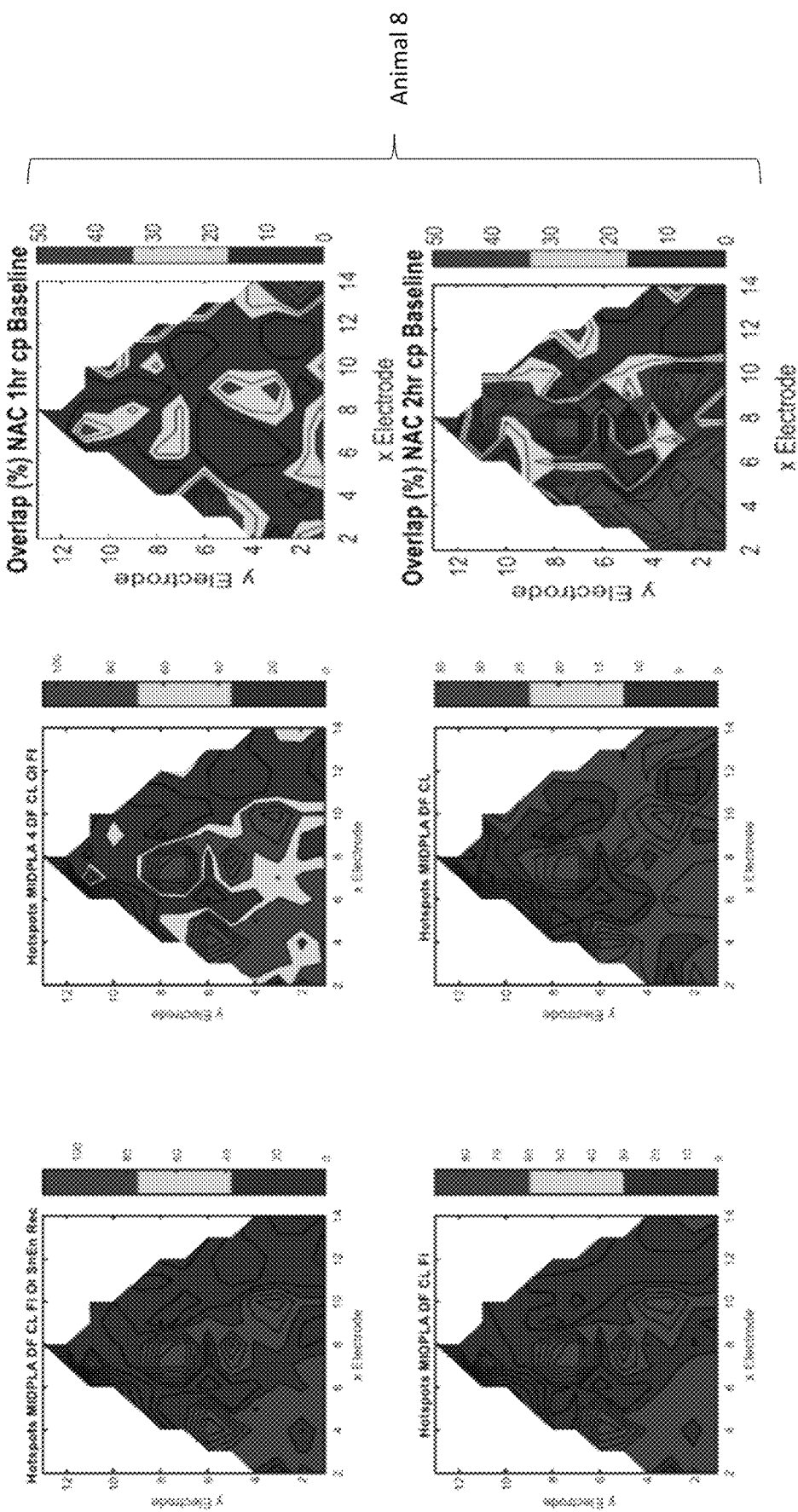
Figure 5C:
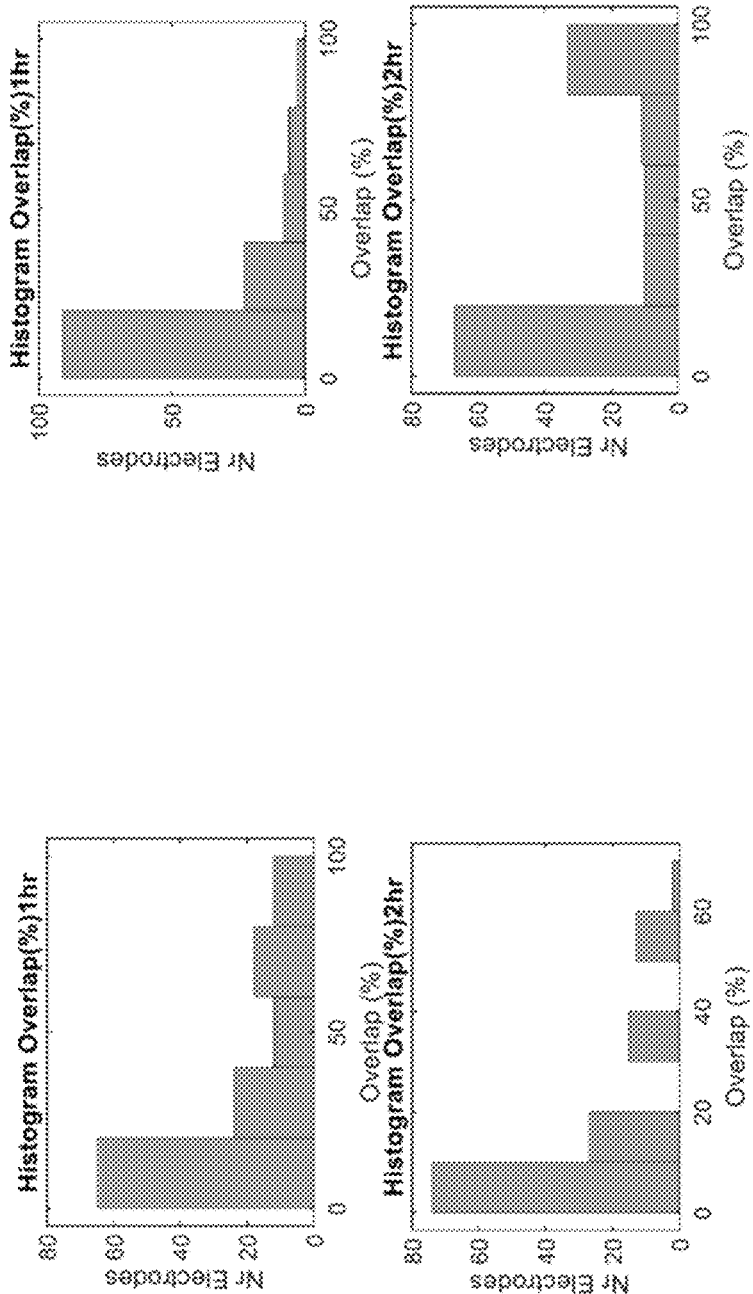
FIG. 5C is a histogram of hotspot overlap in percentage of how many electrogram measures overlap at 1 hour and 2 hours in accordance with an illustrative embodiment.
Figure 5D:
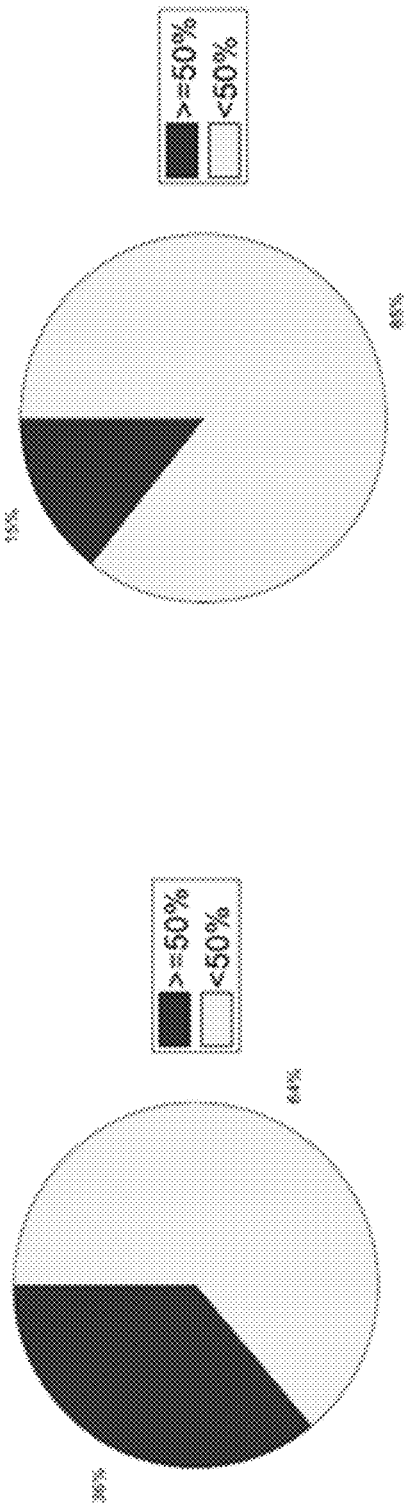
FIG. 5D is a pie chart of hotspot overlap with >50% change in accordance with an illustrative embodiment.
Figure 5D:
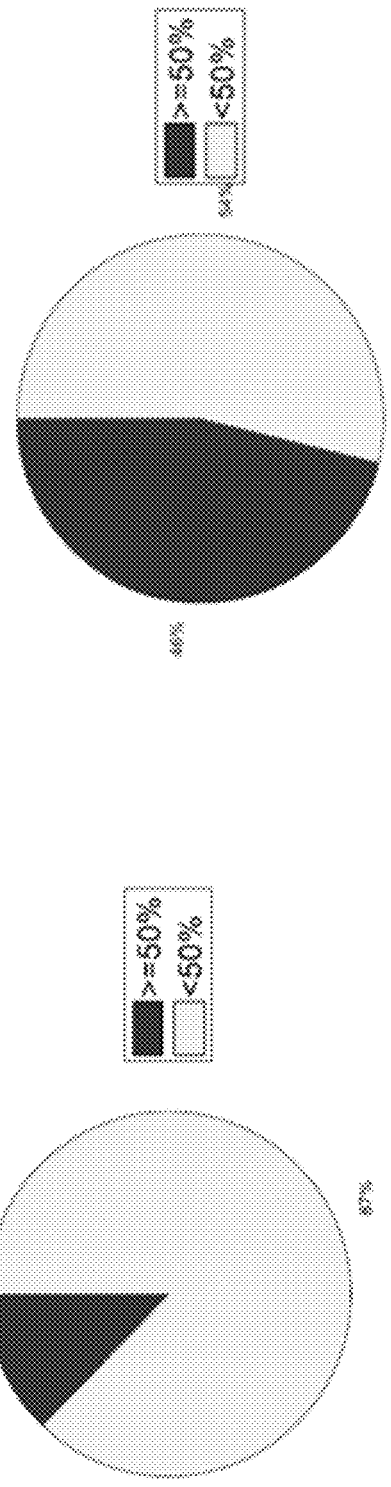
Figure 5E:
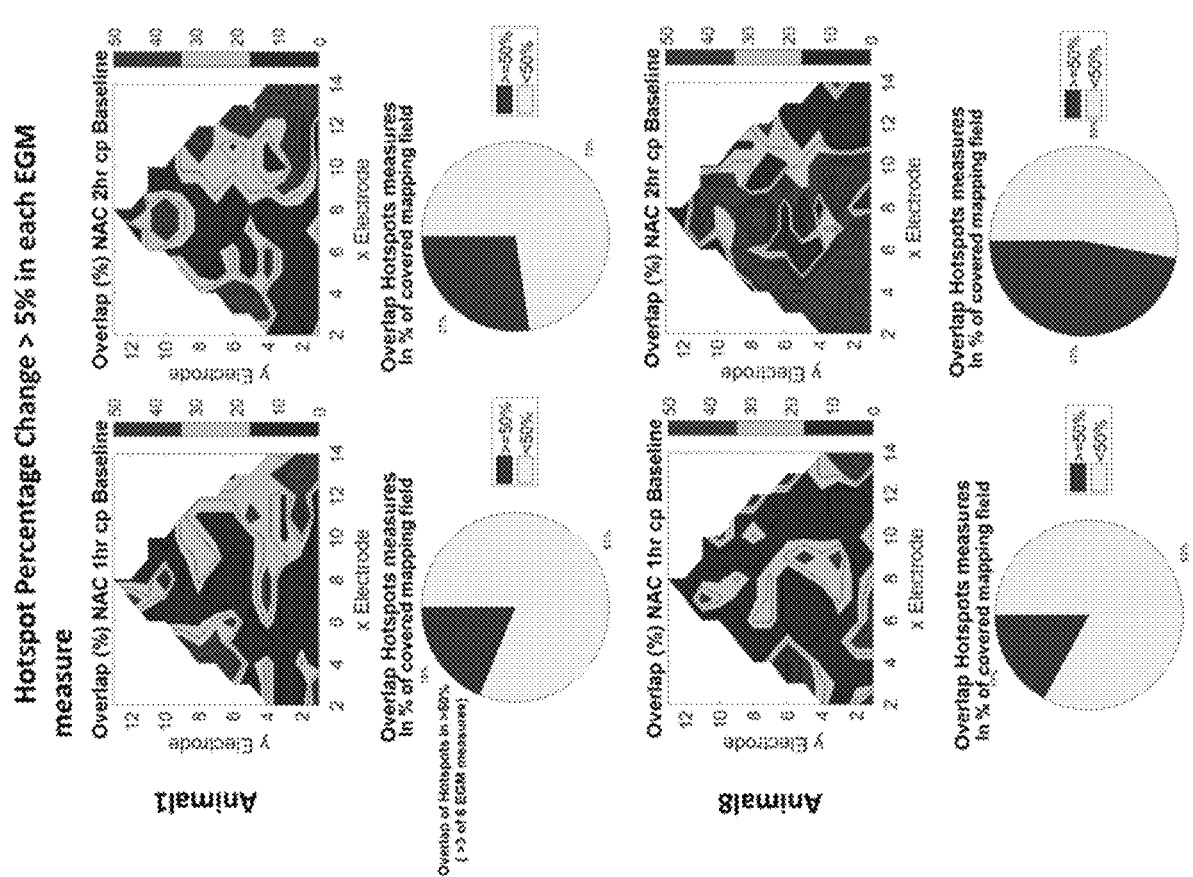
FIG. 5E shows hotspot overlap with hotspots defined as a percentage change of 5% at 1 hour and 2 hours after administration of the ROS scavenger in accordance with an illustrative embodiment.
Figure 5H:
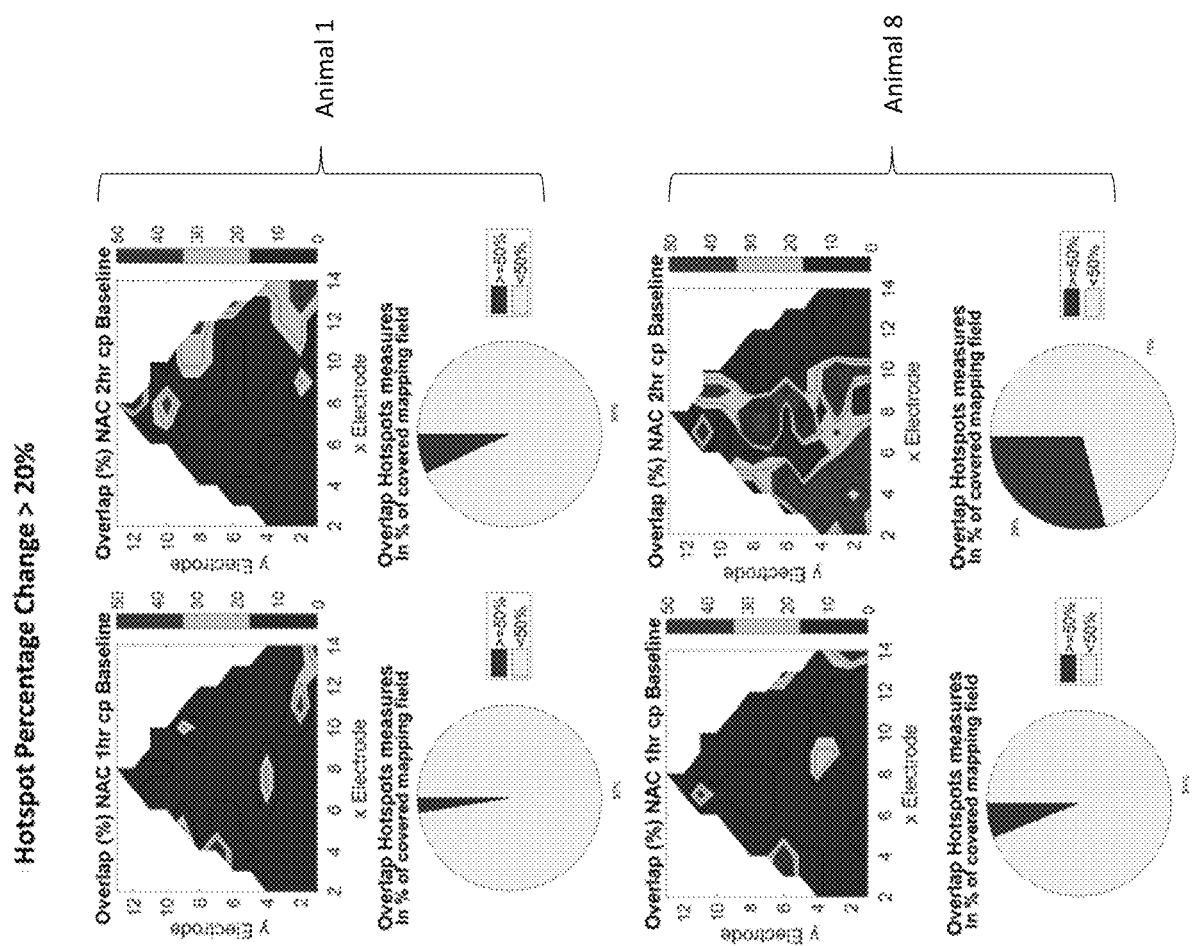
FIG. 5H shows hotspot overlap with hotspots defined as a percentage change of 20% at 1 hour and 2 hours after administration of the ROS scavenger in accordance with an illustrative embodiment.

FIG. 5E shows hotspot overlap with hotspots defined as a percentage change of 5% at 1 hour and 2 hours after administration of the ROS scavenger in accordance with an illustrative embodiment. FIG. 5F shows hotspot overlap with hotspots defined as a percentage change of 10% at 1 hour and 2 hours after administration of the ROS scavenger in accordance with an illustrative embodiment. FIG. 5G shows hotspot overlap with hotspots defined as a percentage change of 15% at 1 hour and 2 hours after administration of the ROS scavenger in accordance with an illustrative embodiment. FIG. 5H shows hotspot overlap with hotspots defined as a percentage change of 20% at 1 hour and 2 hours after administration of the ROS scavenger in accordance with an illustrative embodiment. As shown, using a percentage change threshold of 5%, overlap in more than 50% of the electrogram measurements were detected in 19% and 17% of the mapping field at 1 hour after administration and 27% and 47% at 2 hours after administration in Animals 1 and 8. With a threshold of 20%, only 2% and 7% (Animal 1) and 6% and 29% (Animal 8) (after 1 hour and 2 hours) of the mapping field were covered.

Figure 6A:
FIG. 6A is an isochronal map showing 360 degree rotations in the activation maps in Animal 10 in all regions in accordance with an illustrative embodiment.
Figure 6B:
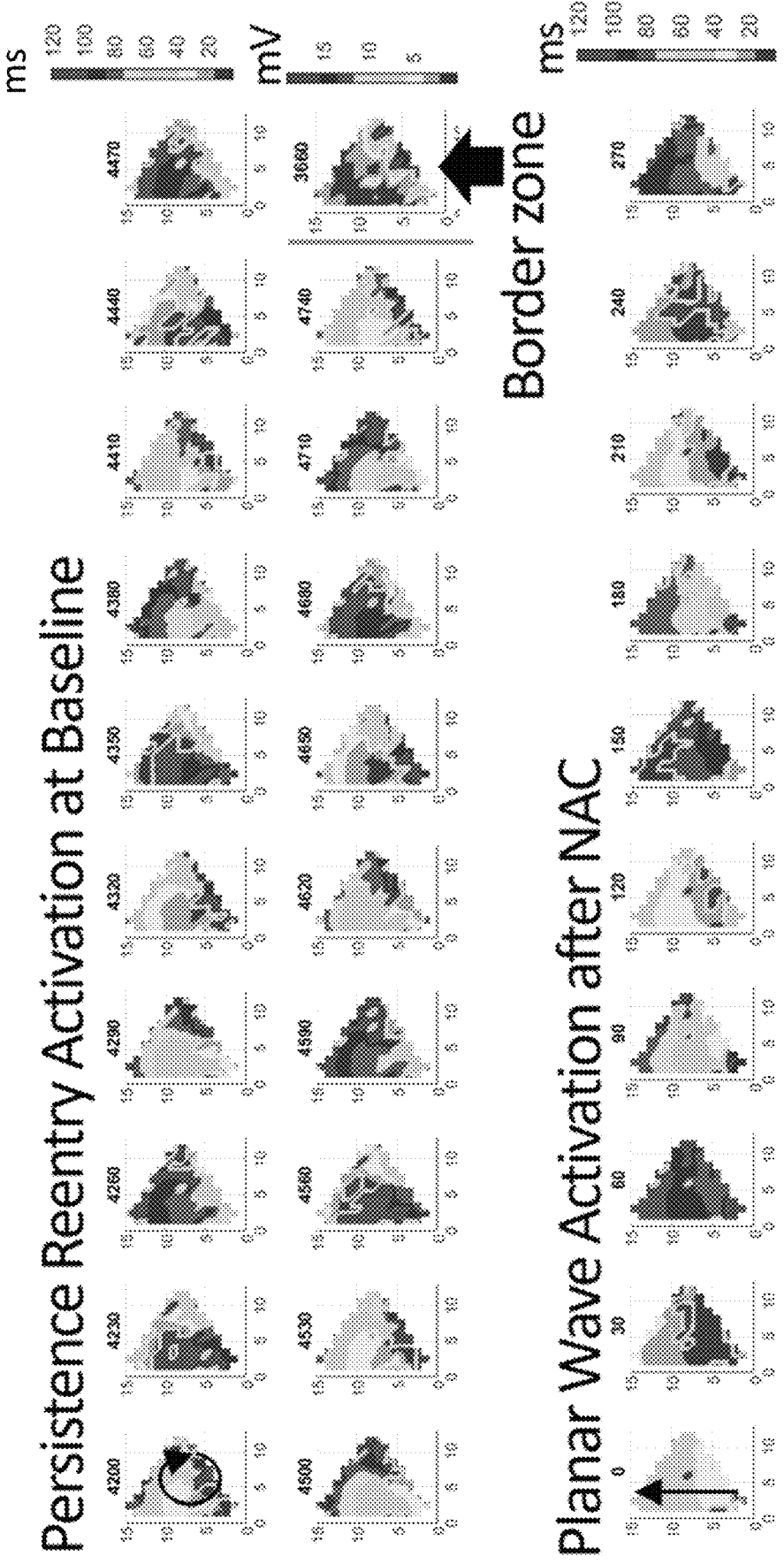
FIG. 6B depicts how NAC administration reduced rotational source in accordance with an illustrative embodiment.
Figure 6C:
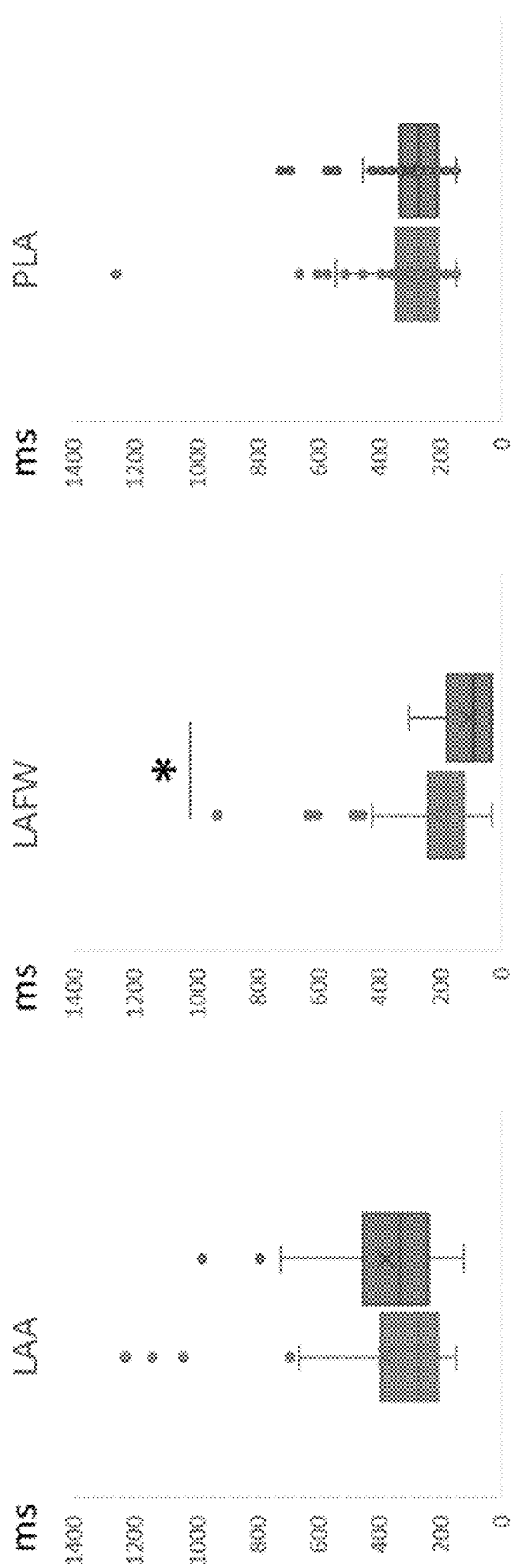
FIG. 6C shows that the stability of observed 360 degree rotations in activation maps significantly decreased after NAC administration in the LAFW in accordance with an illustrative embodiment.

FIG. 6A is an isochronal map showing 360 degree rotations in the activation maps in Animal 10 in all regions in accordance with an illustrative embodiment. FIG. 6B depicts how NAC administration reduced rotational source in accordance with an illustrative embodiment. The marked border zone shows the difference between high and low voltage. The lower portion of FIG. 6B shows a nearly planar activation wave front after NAC administration. FIG. 6C shows that the stability of observed 360 degree rotations in activation maps significantly decreased after NAC administration in the LAFW in accordance with an illustrative embodiment.

Figure 7:
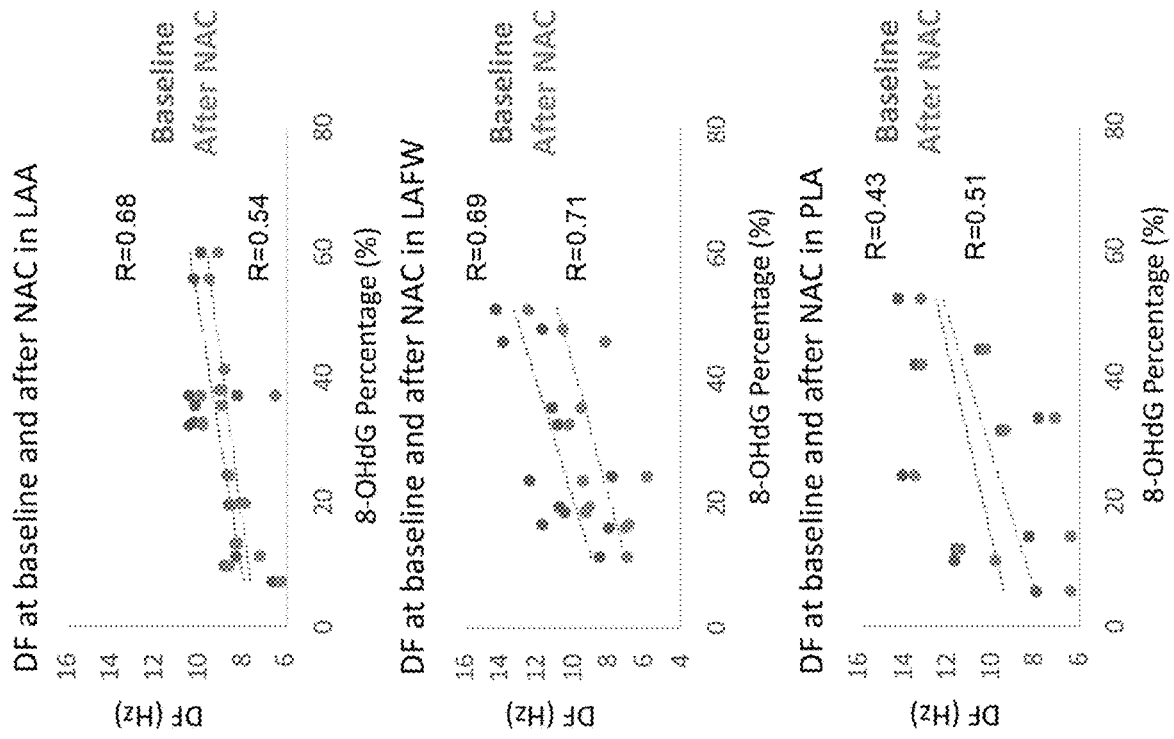
FIG. 7 shows correlation of the characteristic DF at baseline (blue dots), and reduced DF (orange dots) more than 2 hours after administration of the ROS scavenger in accordance with an illustrative embodiment.

FIG. 7 shows correlation of the characteristic DF at baseline (darker shaded dots dots), and reduced DF (lighter shaded dots) more than 2 hours after administration of the ROS scavenger in accordance with an illustrative embodiment. In FIG. 7, the oxidative stress level is given as an 8-OHdG-percentage (%) in the LAA, LAFW, and PLA.

Figure 8A:
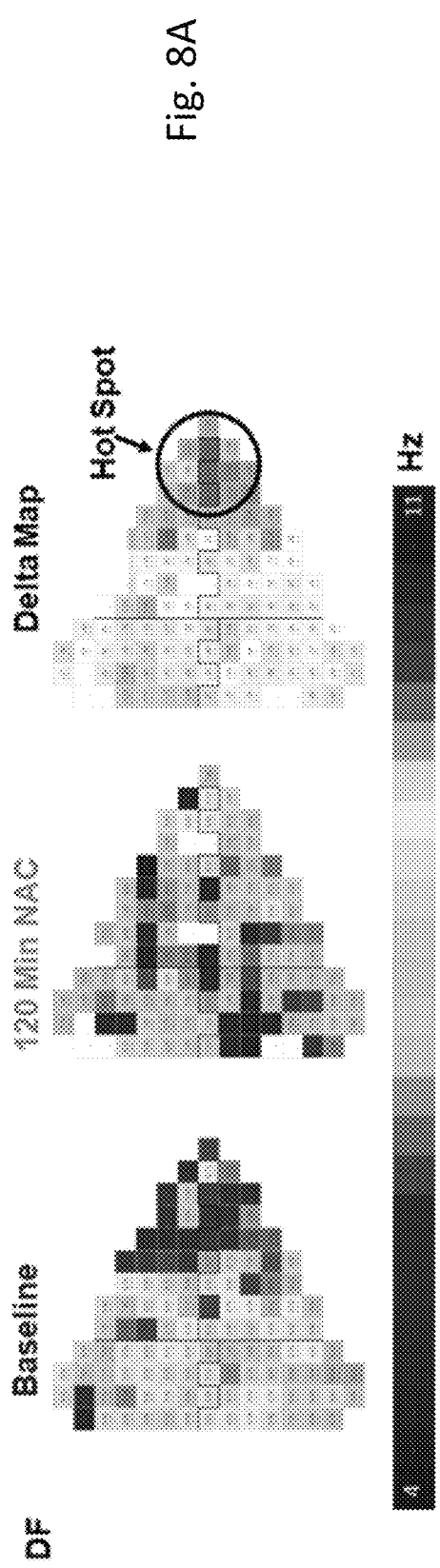
FIG. 8A depicts high density mapping of DF at baseline, 120 minutes after NAC administration, and the corresponding Delta-map depicts the hotspot region with >30% change in DF in accordance with an illustrative embodiment.
Figure 8B:
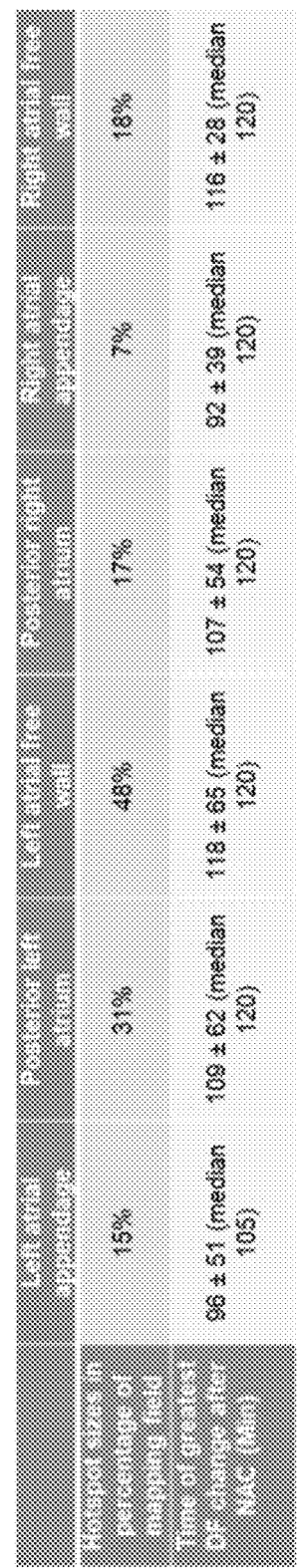
FIG. 8B shows hotspot sizes in percentage of the mapping field having the highest value in the LAFW in accordance with an illustrative embodiment.
Figure 8C:
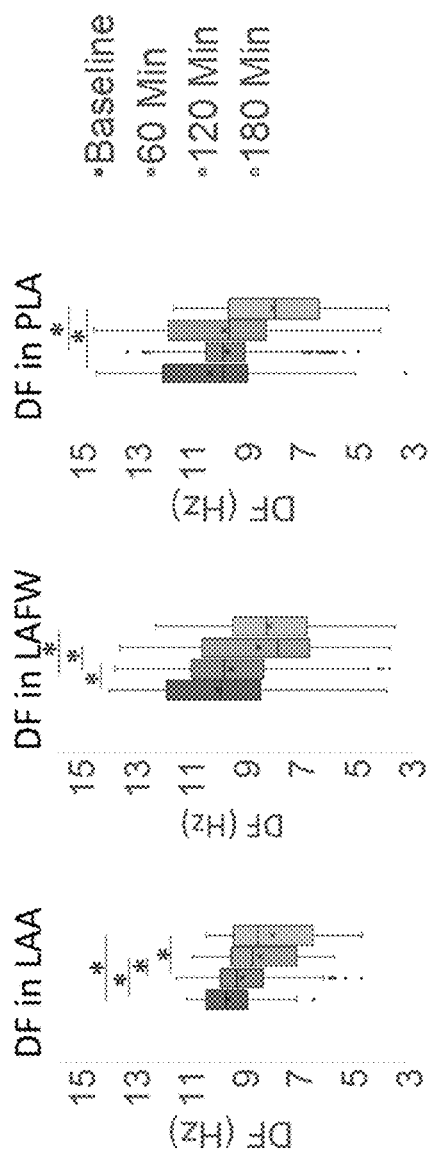
FIG. 8C depicts how the DF decreased over time in hotspot sub regions in accordance with an illustrative embodiment.
Figure 8D:
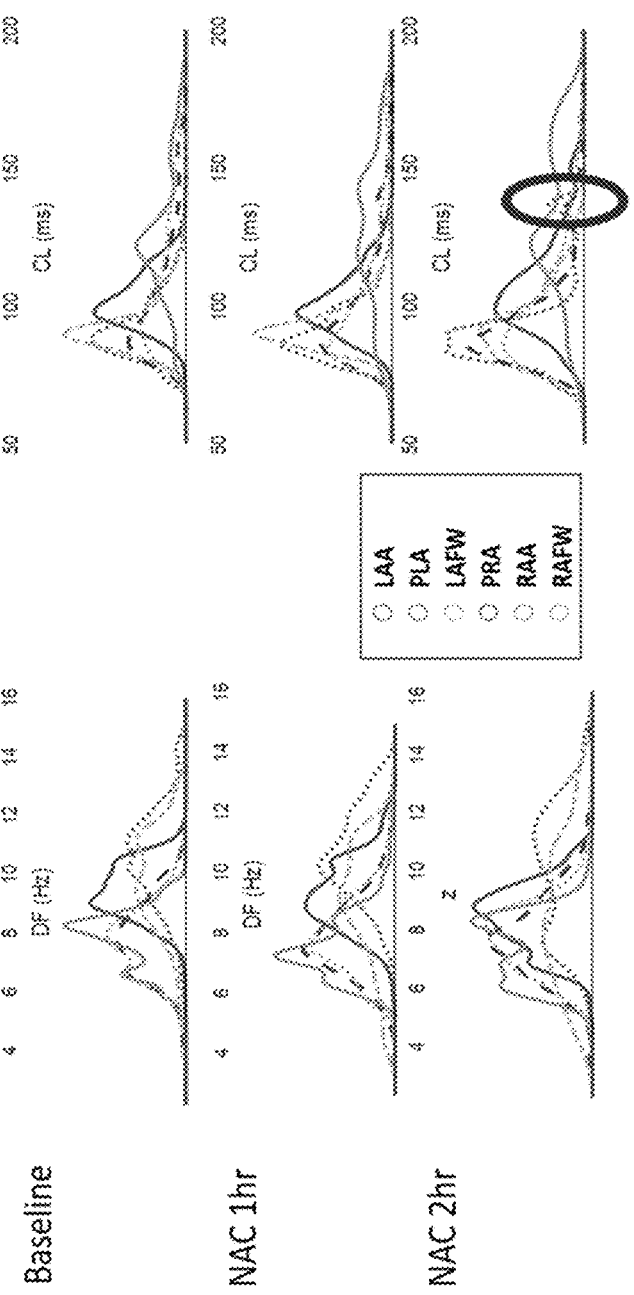
FIG. 8D shows the dominant frequency histogram of all 10 hearts in all 6 atrial regions at baseline, 1 hour after NAC administration, and 2 hours after NAC administration in accordance with an illustrative embodiment.

FIG. 8A depicts high density mapping of DF at baseline, 120 minutes after NAC administration, and the corresponding Delta-map showing the hotspot region with >30% change in DF in accordance with an illustrative embodiment. FIG. 8B shows hotspot sizes in percentage of the mapping field having the highest value in the LAFW in accordance with an illustrative embodiment. As shown, the greatest DF changes after administration of NAC were found at the LAFW after 1 hour. FIG. 8C depicts how the DF decreased over time in hotspot sub regions in accordance with an illustrative embodiment. FIG. 8D shows the dominant frequency histogram of all 10 hearts in all 6 atrial regions at baseline, 1 hour after NAC administration, and 2 hours after NAC administration in accordance with an illustrative embodiment. As shown, most regions had two dominant peaks in DF at baseline. After NAC (1 hour) the DF peak shifted to a lower range of the strongest DF peak in the PLA, LAFW, RAA, PRA, and RAFW. Lower DF values in the low DF range (3-6 Hz) after NAC administration (1 hour and 2 hours) were detected in the LAFW. Also, the DF peak shifted in the LAFW and PLA from 11.5 Hz to 9 Hz (1 hour after NAC) and to 7.5 Hz (2 hours after NAC). The DF peak shifted in the RAA from 8.5 Hz to 7.5 Hz after 1 hr NAC, and the NAC increased CL after 2 hours in the PLA to 140 milliseconds (ms) in a second peak in CL (marked in red).

Thus, it has been shown that acute scavenging of ROS significantly reduces the frequency and complexity of AF in a region dependent and time-dependent manner. The experiments indicate that the extent of change in electrogram characteristics in response to acute ROS inhibition is at least partially driven by the level of oxidative stress in atrial tissue. It follows that OS is an important, dynamic mechanism underlying the formation and maintenance of the AF disease state. The inventors have also shown that acute scavenging of reactive oxygen species significantly reduces AF frequency at discrete and measurable hot spots in the atria, which provides new targets for ablation.

As discussed, any of the operations described herein can be performed by a computing system that includes a processor, memory, transceiver, interface, etc. The memory can store an operating system and computer-readable instructions. Upon execution by the processor, the computer-readable instructions implement the operations described herein. The transceiver is used to receive/transmit data, and the interface allows a user to program and control the system.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A system for treating atrial fibrillation comprising:
   a memory configured to store a baseline measurement of an atrial fibrillation characteristic of a patient and a post administration measurement of the atrial fibrillation characteristic of the patient, wherein the post administration measurement is obtained subsequent to administration of a reactive oxygens species (ROS) scavenger to the patient;
   a processor operatively coupled to the memory and configured to:
      determine a change between the baseline measurement and the post administration measurement of the atrial fibrillation characteristic;

determine an activation pattern responsive to the determined change, wherein the activation pattern includes a number of rotational, focal, and wavelet activities that occur in the patient responsive to administration of the ROS scavenger; and identify, based at least in part on the activation pattern, one or more hot spots of atrial fibrillation, wherein the one or more hot spots comprise target areas for treatment of the atrial fibrillation; and a therapeutic device coupled to the processor, wherein the therapeutic device delivers a therapeutic substance to the one or more identified hot spots.

2. The system of claim 1, further comprising an electrogram system operatively coupled to the processor, wherein the baseline measurement and the post administration measurement are received from the electrogram system.

3. The system of claim 1, wherein the change between the baseline measurement and the post administration measurement comprises a percentage change.

4. The system of claim 1, wherein the processor is further configured to determine changes between baseline measurements and post administration measurements for a plurality of additional atrial fibrillation characteristics.

5. The system of claim 4, wherein the processor is configured to combine the changes between the atrial fibrillation characteristic and the plurality of additional atrial fibrillation characteristics to identify the one or more hotspots.

6. The system of claim 1, wherein the atrial fibrillation characteristic comprises dominant frequency (DF), cycle length (CL), organization index (01), fractionation index (FI), recurrence morphology percentage (Rec %), Shannon's entropy (ShEn), conduction velocity, or voltage.

7. The system of claim 1, wherein the processor is further configured to generate a visualization of a heart of the patient, wherein the visualization depicts the one or more hot spots.

8. The system of claim 1, wherein the processor is configured to compare an amount of the change in the atrial fibrillation characteristic to a characteristic threshold.

9. The system of claim 8, wherein the processor identifies the one or more hot spots as regions in which the amount of change in the atrial fibrillation characteristic exceeds the characteristic threshold.

10. The system of claim 1, wherein the processor determines the change between the baseline measurement and the post administration measurement of the atrial fibrillation characteristic at a plurality of times subsequent to administration of the ROS scavenger to the patient.

11. The system of claim 1, wherein the ROS scavenger comprises N-acetylcysteine.

12. The system of claim 1, wherein the processor is further configured to determine changes between baseline measurements and post administration measurements for a plurality of additional atrial fibrillation characteristics, and wherein the processor is configured to identify an amount of overlap between the atrial fibrillation characteristic and the plurality of additional atrial fibrillation characteristics to identify the one or more hotspots.

13. The system of claim 1, wherein the activation pattern also includes a frequency and stability of the rotational, focal, and wavelet activities that occur in the patient responsive to administration of the ROS scavenger.

14. The system of claim 1, wherein the processor is configured to determine multivariate changes in the atrial fibrillation characteristic, and wherein the one or more hotspots are identified based at least in part on the multivariate changes.

15. A method of treating atrial fibrillation, the method comprising:

storing, in a memory of a computing system, a baseline measurement of an atrial fibrillation characteristic of a patient and a post administration measurement of the atrial fibrillation characteristic of the patient, wherein the post administration measurement is obtained subsequent to administration of a reactive oxygens species (ROS) scavenger to the patient;

determining, by a processor operatively coupled to the memory, a change between the baseline measurement and the post administration measurement of the atrial fibrillation characteristic;

determining, by the processor, an activation pattern responsive to the determined change, wherein the activation pattern includes a number of rotational, focal, and wavelet activities that occur in the patient responsive to administration of the ROS scavenger;

identifying, by the processor and based at least in part on the determined activation pattern, one or more hot spots of atrial fibrillation, wherein the one or more hot spots comprise target areas for treatment of the atrial fibrillation; and delivering, by a therapeutic device coupled to the processor, a therapeutic substance to the one or more identified hot spots.

16. The method of claim 15, further comprising:

determining, by the processor, changes between baseline measurements and post administration measurements for a plurality of additional atrial fibrillation characteristics; and combining the changes between the atrial fibrillation characteristic and the plurality of additional atrial fibrillation characteristics to identify the one or more hotspots.

17. The method of claim 15, further comprising generating, by the processor, a visualization of a heart of the patient, wherein the visualization depicts the one or more hot spots.

18. The method of claim 15, further comprising comparing, by the processor, an amount of the change in the atrial fibrillation characteristic to a characteristic threshold, and wherein the processor identifies the one or more hot spots as regions in which the amount of change in the atrial fibrillation characteristic exceeds the characteristic threshold.

* * * * *